United States Patent [19]

Stobie

[11] Patent Number: 5,292,749
[45] Date of Patent: Mar. 8, 1994

[54] ANTIMUSCARINIC BRONCHODILATORS

[75] Inventor: Alan Stobie, Deal, England

[73] Assignee: Pfizer Inc., New York, N.Y.

[21] Appl. No.: 852,261

[22] Filed: Jun. 5, 1992

[30] Foreign Application Priority Data

Sep. 6, 1990 [GB] United Kingdom ............... 9019472
Mar. 28, 1991 [GB] United Kingdom ............... 9106733

[51] Int. Cl.$^5$ ................ C07D 453/00; A61K 31/435
[52] U.S. Cl. .................................. 514/305; 514/826; 546/137
[58] Field of Search ............... 546/137; 514/305, 826

[56] References Cited

U.S. PATENT DOCUMENTS

| | | | |
|---|---|---|---|
| 3,290,316 | 12/1966 | Stempel | 546/137 |
| 3,714,357 | 1/1973 | Gueremy et al. | 546/137 |
| 3,833,592 | 9/1974 | Papanastassiou | 546/137 |
| 4,431,627 | 2/1984 | Eckelman et al. | 546/137 |
| 4,644,003 | 2/1987 | Rzeszotarski et al. | 546/137 |
| 4,843,074 | 6/1989 | Rzeszotarski et al. | 546/137 |
| 4,970,315 | 11/1990 | Schmidhalter | 546/137 |
| 4,988,691 | 1/1991 | Benelli et al. | 546/137 |

FOREIGN PATENT DOCUMENTS 0424021 4/1991 European Pat. Off. .
1935751 2/1970 Fed. Rep. of Germany .

OTHER PUBLICATIONS

Chemical Abstracts, vol. 96, No. 5, 1 Feb. 1982 (Columbus, Ohio, US) E. E. Mikhlina et al.: "Synthesis and cholinolytic properties of 3-hydroxyquinuclidine esters", see p. 647, abstract 35045c, & Khim.-Farm.Zh. 1981, 15(8), 51–5.

J. Med. Chem., vol. 26, 1983, E. R. Atkinson et al.: "Parasympatholytic (anticholinergic) esters of the isomeric 2-tropanols. 2. Non-glycolates", see pp. 1772–1775, especially compound 17.

Primary Examiner—Marianne M. Cintins
Assistant Examiner—Catherine Scalzo
Attorney, Agent, or Firm—Peter C. Richardson; Paul H. Ginsburg; Philip C. Strassburger

[57] ABSTRACT

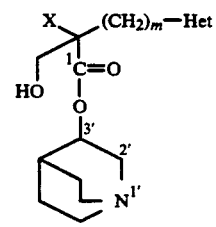

3-Quinuclidinyl butanoate and propanoate antimuscarinic bronchodilators, particularly useful in the treatment of chronic obstructive airways disease and asthma, of formula (1), and their pharmaceutically acceptable salts, wherein X is either (a) a phenyl group optionally substituted by one or two substituents each independently selected from halo, $CF_3$, $C_1$–$C_4$ alkyl, $C_1$–$C_4$ alkoxy and hydroxy or (b) a thienyl group; and "Het" is either (a) a 5-membered nitrogen-containing heterocyclic group attached to the adjacent carbon atom either by a carbon or a ring nitrogen atom and which is selected from imidazolyl, pyrazolyl, triazolyl and tetrazolyl. (b) an oxadiazolyl or thiadiazolyl group attached to the adjacent carbon atom by a carbon atoms, or (c) a 6-membered nitrogen-containing heterocyclic group attached to the adjacent carbon atom by a carbon atom and selected from pyridinyl, pyrazinyl, pyrimidinyl and pyridazinyl, "Het" being optionally substituted by up to two substituents each independently selected from halo, $CF_3$, $C_1$–$C_4$ alkyl, $C_1$–$C_4$ alkoxy, hydroxy, amino and azido; and m is 1 or 2.

14 Claims, No Drawings

ANTIMUSCARINIC BRONCHODILATORS

BACKGROUND OF THE INVENTION

This invention relates to 3-quinuclidinyl butanoates and propanoates and which are lung-selective antimuscarinic bronchodilators. Thus these compounds are particularly useful in the treatment of chronic obstructive airways disease (COAD) and asthma.

COAD is a term encompassing conditions which exhibit, to differing extents, several major progressively developing clinicopathological features, namely inflammatory swelling of airway walls, hypertrophy of submucosal glands, and hyperplasia of epithelial secretory cells leading to hypersecretion of viscous mucous which cannot be cleared effectively, progressive increase in irreversible bronchospasm and decrease in lung elastic recoil. This complex pathway results in progressive loss of lung function, with respiratory impairment, increasing morbidity and, finally, death.

Thus, COAD, and also asthma, are disease of reduced lung function in which antimuscarinic bronchodilators are known to improve airway patency. However, existing agents are non-selective for smooth muscle muscarinic sites in lung and this reduces their effectiveness as bronchodilators and leads to unwanted side effects. Sub-types of muscarinic receptor are now known to exist in the airways (see P. J. Barnes, P. Minette and J. Maclagan, TIPS, 1988, 9, 412.); M1 receptors are present on sympathetic nerves and parasympathetic ganglia; M2 receptors on pulmonary cholinergic nerves (prejunctional inhibitory receptors) and M3 receptors are located on smooth muscle (post-junctional receptors). The compounds of the present invention generally have bronchospasmolytic effects at doses which do not significantly affect receptors in other tissues such as brain, heart, gastro-intestinal tract, eye and salivary gland. Furthermore, they generally show selectivity for the lung post-junctional M3 receptors as opposed to the pulmonary pre-junctional M2 receptors and cardiac M2 receptors. Therapeutic action at some other smooth muscle sites may be envisaged. For example, the compounds are also likely to be useful in treating urinary incontinence.

SUMMARY OF THE INVENTION

Thus the present invention provides a compound of the formula;

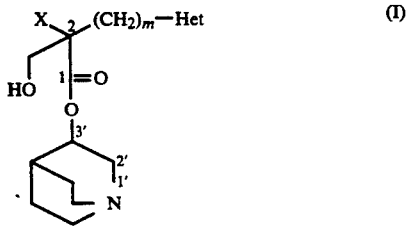

(I)

or a pharmaceutically acceptable salt thereof, wherein X is either (a) a phenyl group optionally substituted by 1 or 2 substituents each independently selected from halo, $CF_3$, $C_1$-$C_4$ alkyl, $C_1$-$C_4$ alkoxy and hydroxy or (b) a thienyl group; and "Het" is either (a) a 5-membered nitrogen-containing heterocyclic group attached to the adjacent carbon atom either by a carbon or a ring nitrogen atom and which is selected from imidazolyl, pyrazolyl, triazolyl and tetrazolyl, or (b) an oxadiazolyl or thiadiazolyl group attached to the adjacent carbon atom by a carbon atom, or (c) a 6-membered nitrogen-containing heterocyclic group attached to the adjacent carbon atom by a carbon atom and selected from pyridinyl, pyrazinyl, pyrimidinyl and pyridazinyl, "Het" being optionally substituted by up to 2 substituents each independently selected from halo, $CF_3$, $C_1$-$C_4$ alkyl, $C_1$-$C_4$ alkoxy, hydroxy, amino and azido; and m is 1 or 2.

"Halo" means F, Cl, Br or I. $C_3$ and $C_4$ alkyl and alkoxy groups can be straight or branched chain.

X is preferably either (a) a phenyl group optionally substituted by 1 or 4 fluoro atoms or (b) a 3-thienyl group. X is most preferably an unsubstituted phenyl group.

"Het" thus includes, for example, 1H-imidazol-1-yl, 2-azido-1H-imidazol-1-yl, 2-amino-1H-imidazol-1-yl, 2-methyl-1H-imidazol-1-yl, 4-methyl-1-H-imidazol-1-yl, imidazol-2-yl, 1-methylimidazol-2-yl, 1H-1,2,3-triazol-1yl, 1-methyl-1,2,3-triazol-5-yl, 1H-1,2,4-triazol-1-yl, 3-bromo-5-methyl-1H-1,2,4-triazol-1-yl, 3-bromo-5-ethyl-1H-1,2,4-triazol-1-yl, 3bromo-5-propyl-1H-1,2,4-triazol-1-yl, 3-bromo-5-isopropyl-1H-1,2,4-triazol-1-yl, 3-bromo-1-isobutyl-1H-1,2,4-triazol-1-yl, 5-methyl-1H-1,2,4-triazol-1-yl, 5-ethyl-1H-1,2,4-triazol-1yl, 5-propyl-1H-1,2,4-triazol-1-yl, 5-isopropyl-1H-1,2,4-triazol-1-yl, 5-isobutyl-1H-1,2,4-triazol-1-yl, 3-chloro-1H-1,2,4-triazol-1-yl, 1H-1,2,5-triazol-1-yl, 1H-pyrazol-1-yl, 1-methyl-pyrazol-5-yl, 1H-tetrazol-1-yl, 1-methyltetrazol-5-yl, 2-methyl-tetrazol-5-yl, 1H-imidazol-4(5)-yl, 1H-pyrazol-4-yl, 1H-pyrazol-3(5)-yl, pyridin-2-, 3- or 4-yl, pyrazin-2-yl, pryimidin-2-yl, pyrimidin-4-yl, 3-methyl-1,2,4-oxadiazol-5-yl, pyridazin-3-yl or pyridazin-4-yl.

"Het" is most preferably an imidazolyl, pyrazolyl, triazolyl, tetrazolyl, oxadiazolyl, pyridinyl, pyrimidinyl or pyridazinyl group, all said group being optionally substituted by one or two substituents each selected from $C_1$-$C_4$ alkyl and halo (preferably chloro or bromo).

When m is 1, "Het" is most preferably a 1H-imidazol-1-yl, 1H-1,2,4-triazol-1-yl or 5-methyl-1H-1,2,4-triazol-1-yl group When m is 2, "Het" is most preferably a 1-methylimidazol-2-yl group.

Those skilled in the art will appreciate that there are two asymmetric centres in the compounds (I), namely those at the positions identified as 2- and 3'- in FIG. (1). All diastereoisomers whether separated or not are within the scope of this invention. The preferred esters are however the 3R-quinuclidinyl esters.

When m is 1, the preferred sterochemistry at position 2 is R. When m is 2, the preferred sterochemistry at position 2 is S. Thus the preferred compounds are either (2R, 3R) 3-quinuclidinyl propanoates or are (2S, 3R) 3-quinuclidinyl butanoates, and can be represented as follows:

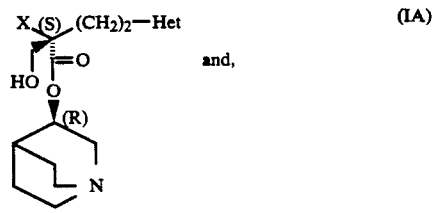

(IA)

and,

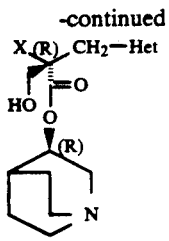

DETAILED DESCRIPTION OF THE INVENTION

The compounds of the formula (I) are preparable by the following routes:

Route A

The compounds of the formula (I) can be prepared by the reaction of an ester of the formula (II) with formaldehyde in the presence of a strong base such as lithium or potassium diisopropylamide, potassium t-butoxide or sodium hydride. The strong base reacts with the ester (II) to form the carbanion (IIA), and the carbanion then reacts with the formaldehyde. The formaldehyde is generally provided either as formaldehyde gas, or as paraformaldehyde (which breaks down to formaldehyde in solution).

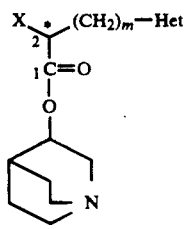

The carbanion has the formula:

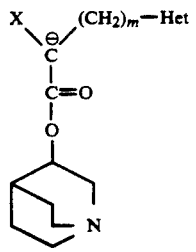

The preferred techniques are as follows.

In the preferred technique, sodium hydride or potassium t-butoxide, the ester (II) and paraformaldehyde are reacted together in a suitable organic solvent, e.g. dimethylformamide, at about room temperature. The product (I) can then be isolated and purified conventionally.

In an alternative technique, the ester (II) is reacted for a few hours with lithium diisopropylamide in tetrahydrofuran at about −78° C. The reaction mixture is then slowly allowed to warm at room temperature during which time formaldehyde gas, generated e.g. by heating paraformaldehyde, is intermittently passed into the solution. Alternatively, paraformaldehyde is simply added to the solution.

Compounds (I) having R stereochemistry at position 3' are preferred, and these are best obtained by starting with an ester (II) having R stereochemistry at position 3' in formula (II). Likewise the 3S quinuclidinyl esters can be prepared from esters (II) having S stereochemistry at the 3'-position.

It is usually most convenient to start with the 2RS forms of the esters (II) even if the 2R or 2S, rather than 2RS, end products are required. This will result in a mixture of diastereomers of the compounds (I), and, if desired, these can be separated into the 2R and 2S forms by conventional techniques such as fractional crystallization or chromatography. As stated above, in general, when m is 1, the (2R, 3R), and when m is 2, the (2S, 3R), forms of the compounds (I) are preferred.

The novel esters (II) also form a part of the invention.

The starting materials (II) in which m is 1 are obtainable by conventional techniques, e.g. as follows:

(a) This route is generally only suitable for preparing intermediates in which "Het" is a 6-membered heterocycle as previously defined.

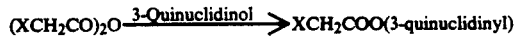

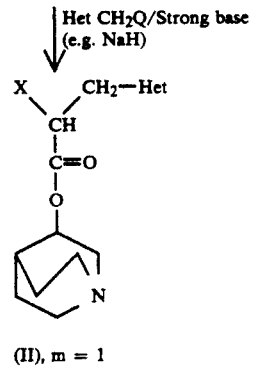

Q is a suitable leaving group, typically Cl or Br.

(b) This route is generally only suitable for preparing intermediates in which "Het" is either a 6-membered heterocycle or a 5-membered heterocycle linked via carbon to the adjacent carbon atom.

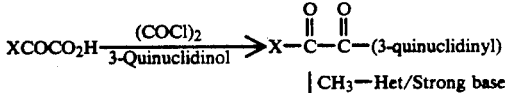

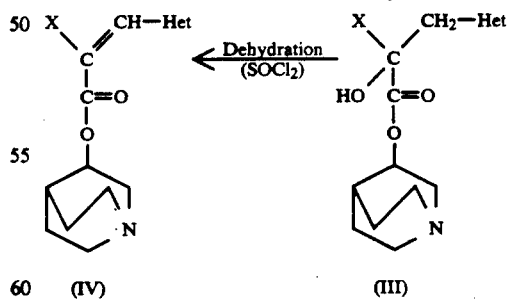

Compounds (II), m = 1.

It is preferred to use (R)-3-quinuclidinol in the above so as to obtain the preferred (R)-stereochemistry at the 3'-position.

and (c)

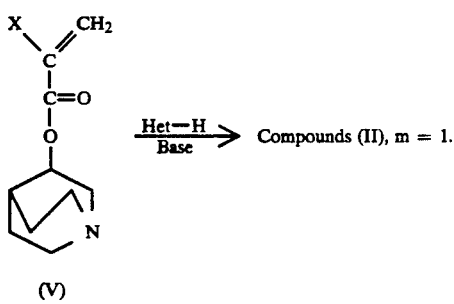

(V)

Het—H / Base → Compounds (II), m = 1.

The compounds (V) can be prepared as described in Route B.

Route B

This reaction can be illustrated as follows:

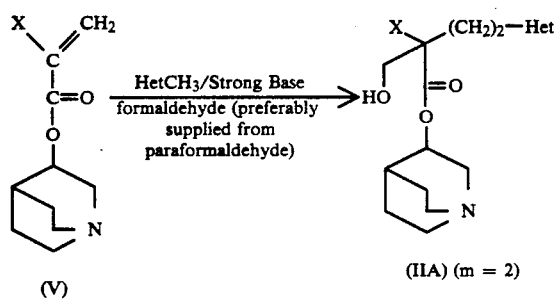

The reaction also proceeds via the carbanion (IIA) (m=2)—see Route A—but it is not necessary to isolate it.

The reaction can be carried out conventionally. The anion of the heterocycle Het-CH$_3$ can be obtained conventionally by reaction of said heterocycle with a base, preferably a strong base such as n-butyllithium or lithium or potassium diisopropylamide.

The preferred technique is to react the heterocycle Het-CH$_3$ with n-butyllithium or lithium diisopropylamide in a suitable organic solvent, e.g. tetrahydrofuran, at about −78° C. After a few hours, the quiuclidine derivative (V) in a suitable organic solvent, e.g. tetrahydrofuran, is added, and the reaction mixture is stirred at −78° C. for a half hour or so and then paraformaldehyde is added and the mixture is allowed to warm slowly to room temperature. After a few hours the desired product (I) is recovered from the reaction mixture by conventional techniques.

The starting materials (V) can be obtained conventionally, e.g. as follows:

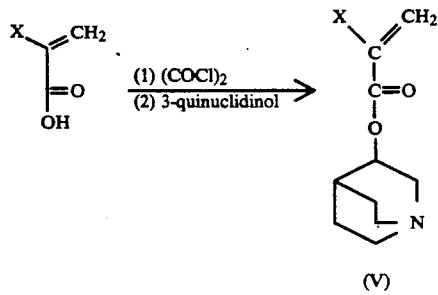

Again it is preferred to use (R)-3-quinuclidinol.

Route C

This reaction can be illustrated as follows:

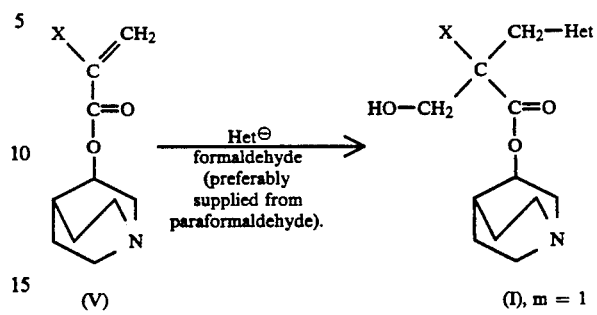

The reaction also proceeds via the carbanion (IIA) (m=1)—see Route A—but it is not necessary to isolate it.

This route is only suitable for preparing the compounds (I) in which m is 1 and "Het" is (i) a 5-membered heterocycle attached to the adjacent carbon atom by a ring nitrogen atom or (ii) a 5-membered heterocycle attached to the adjacent carbon atom by a carbon atom and containing no hydrogen atoms on any of its ring nitrogen atoms (see e.g. Examples 26–28), or (iii) pyridyl.

The reaction can be carried out conventionally. The anion of the heterocycle Het-H can be obtained conventionally by reaction of said heterocycle with a base, preferably a strong base such as sodium hydride, n-butyllithium, or lithium or potassium diisopropylamide or potassium t-butoxide. Pyridine anions are best prepared by reaction of the appropriate bromopyridine with n-butyllithium as is known to those skilled in the art. The formaldehyde can be provided as formaldehyde gas, or as paraformaldehyde which breaks down to formaldehyde in solution.

For preparing compounds in which m is 1 and "Het" is attached via a ring-nitrogen atom to the adjacent carbon atom. the preferred technique is to react the quinuclidine derivative of the formula (V), paraformaldehyde, the heterocycle Het-H and sodium hydride together in a suitable organic solvent, e.g. dimethylformamide, at about room temperature. The product can then be isolated and purified conventionally.

For preparing compounds in which m is 1 and "Het" contains no hydrogen atoms on its ring nitrogen atoms and is attached by a carbon atom to the adjacent carbon atom, the preferred technique is to react the heterocycle Het-H with n-butyllithium in a suitable organic solvent, e.g. tetrahydrofuran, at about −78° C. After a few hours, the quinuclidine derived (V) in a suitable organic solvent, e.g. tetrahydrofuran, is added, and the reaction mixture is stirred at −78° C. for a half hour or so and then allowed to warm slowing to about 0° C. when paraformaldehyde is added. After a few hours the desired product (I) is recovered from the reaction mixture by conventional techniques.

In instances where tautomerism occurs in the heterocycle, then more than one anion may be generated by the reaction of the heterocycle with the base, thus producing a mixture of products as in Example 5.

Some of the compounds of the formula (I) (m=1 or 2) can be prepared from other compounds of the formula (I). For example, an azido-substituent on "Het" can be reduced to amino e.g. by catalytic hydrogenation, and a bromo-substituent on "Het" can be reduced to hydrogen again by catalytic hydrogenation. A typical hydrogenation is carried out in ethanol at about 50 psi (344.7 kPa) hydrogen pressure in the presence of palladium-on-carbon at about room temperature.

The selectivity of the compounds as muscarinic receptor antagonists can be measured as follows.

Male guinea pigs are sacrificed and the ileum, trachea, bladder and right atrium are removed and suspended in Krebs solution under a resting tension of 1 g at 30° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating double atria is derived from isometrically recorded contractions.

Dose-response curves to carbachol are determined using a 1-5 minute contact time for each dose of agonist until the maximum response is achieved. The organ bath is drained and refilled with Krebs solution containing the lowest dose of the test compound. The test compound is allowed to equilibrate with the tissue for 20 minutes and the agonist dose-response curve is repeated until the maximum response is obtained. The organ bath is drained and refilled with Krebs solution containing the second concentration of test compound and the above procedure is repeated. Typically three concentrations of the test compound are evaluated on each tissue.

The negative log of the molar contraction ($pA_2$) of the test compound which causes a doubling of the agonist concentration to produce the original response is determined by Schild analysis (Arunlakshana and Schild (1959), Brit. J. Pharmacol., 14, 48-58). Using the above pharmacological techniques, tissue selectivity for muscarinic receptor antagonists is determined.

Activity against agonist-induced or nerve-evoked bronchoconstriction, gut or bladder contractility in comparison with changes in heart rate is determined in the anaesthetised dog, cat or guinea pig. Oral activity is assessed in the conscious dog determining compound effects on, lung function, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

The selectivity of the compounds for pulmonary post-injunctional as against pre-junctional muscarinic receptors in anaesthetised guinea pigs and cats can be assessed by the following techniques. Acetylcholine released by nerve stimulation activates post-junctional M3 muscarinic receptors to cause contraction or airway smooth muscle and, in addition, activates pre-junctional autoreceptors which inhibit further transmitter release. Animal studies indicate that these pulmonary per-junctional muscarinic autoreceptors are of the M2 subtype (Barnes et al, 1989). Non-selective agents like ipratropium bromide will inhibit both sites, resulting, in the case of nerve-mediated responses, in an increase in transmitter release which can overcome the post-junctional receptor blockade. Published literature has shown that ipratropium bromide can actually potentiate vagally-induced bronchoconstriction in anaesthestised guinea pigs (Fryer and Maclagan, Eur. Jou. Pharmacol., 139, 187-191 (1987)). Thus, the effects of the test compounds on pre- and post- junctional muscarinic sites can be determined in vivo by comparing the effect on nerve mediated responses with the effect on responses to exogenously administered acetylcholine.

For example, the compound of Example 1 has been found to antagonise both acetylcholine-induced, and vagally-induced, bronchoconstriction in anaesthetised guinea pigs over the same dose range. This contrasts with opratropium bromide which is significantly less potent against vagally-induced than against acetylcholine-induced bronchoconstriction. Additionally, at doses below 1 $\mu g/kg$ of ipratropium bromide, vagally-induced bronchoconstriction is actually potentiated, confirming its pre-junctional effects.

Similar results were obtained from the compound of Example 1 in the anaesthetised cat. The animals were pretreated with propranolol because high sympathetic tone under chloroalose anaesthesia may oppose potentiation of vagus nerve-induced bronchoconstriction. The test results indicate that, in addition to its high potency, the compound of Example 1, in contrast to ipratropium bromide, does not interrupt negative feedback control of transmitter relase in both guinea-pig and cat. This confirms the demonstrated in vitro selectivity of this compound for M3 as opposed to M2 muscarinic receptors.

As a result of this selectivity for post- as opposed to pre-junctional muscarinic receptors, the compounds of the invention should be more effective bronchodilators in respiratory disease compared to ipratropium bromide.

The acid addition salts of the compounds of formula (I) can be prepared in a conventional manner by treating a solution or suspension of the free base of (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, ascorbic, benzoic, cinnamic, fumaric, sulfuric, phosphoric, hydrochloric, hydrobromic, hydroiodic, sulfamic, sufonic such as methanesulfonic, benzenesulfonic, and related acids.

For treatment of the various conditions described above the compounds of formula (I) may be administered to a subject in need of treatment by a variety of conventional routes of administration, including oral administration, and in an aerosol or dry powder composition for administration by inhalation. The compounds have potential for absorption through the gastro-intentstinal tract and thus administration by slow release formulations is also possible.

In general, a therapeutically-effective oral dose for the active compounds of formula (I) is likely to range from 0.01 to 1 mg/kg body weight of the subject to be treated, preferably 0.1 to 0.5 mg/kg. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Although the compounds of formula (I) can be administered alone, they will generally be administered in admixture with a pharmaceutical carrier selected with regard to the intended route of administration and standard pharmaceutical practice. For example, oral administration may be in the form of tablets containing such excipients as starch or lactose, in capsules either alone or in admixture with excipients, in aerosol or dry powder inhaler form, or in the form of elixirs or suspensions containing flavouring or colouring agents.

In a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I) or a pharmaceutically acceptable salt thereof, for use as a medicament.

The invention further includes the use of a compound of the formula (I), or of a pharmaceutically acceptable salt thereof, for the manufacture of a medicament for the treatment of chronic obstructive airways disease or asthma.

The following Examples illustrate the preparation of the compounds of the formula (I):

EXAMPLE 1

(R)-3-Quinuclidinyl (R and S)-3-hydroxy-2-(1H-imidazol-1-ylmethyl)-2-phenyl-propanoate

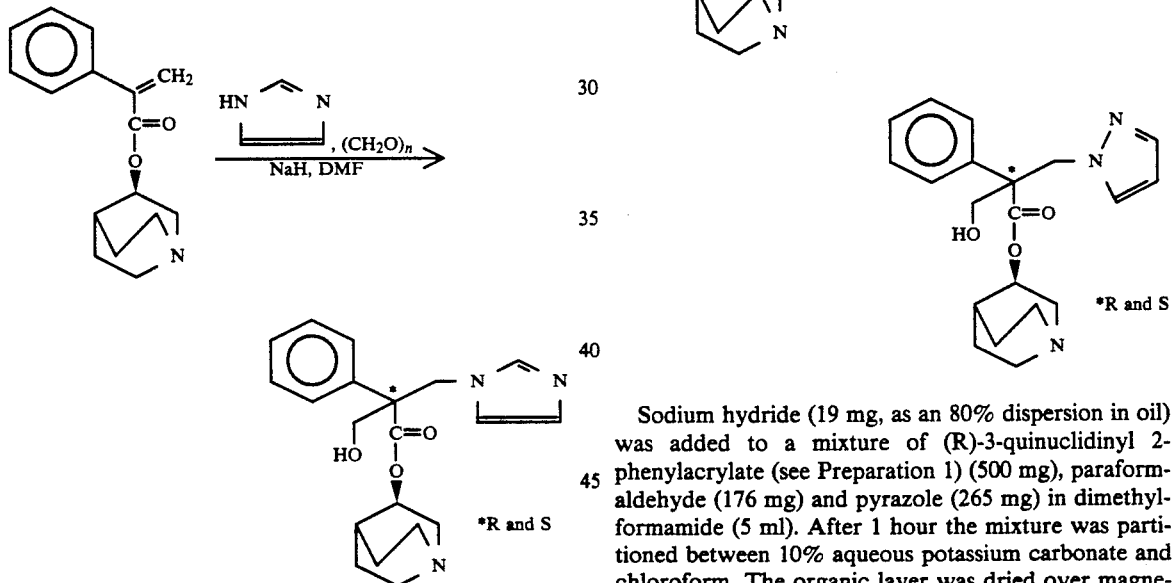

Sodium hydride (10 mg of an 80% dispersion in oil) was added to a mixture of (R)-3-quinuclidinyl 2-phenylacrylate (see Preparation 1) (257 mg), paraformaldehyde (90 mg) and imidazole (100 mg) in dimethylformamide (5 ml) at room temperature. After 1 hour the mixture was partitioned between 10% aqueous potassium carbonate and chloroform. The organic layer was dried over magnesium sulphate and evaporated to leave a residue which was purified by chromatography on silica gel, performing a gradient elution using ethyl acetate/ether/diethylamine (50:50:5) plus methanol (5→10%) as eluant. Fractions containing the first eluted diastereoisomer were combined, evaporated and treated with ethereal hydrogen chloride to give the title compound as a dihydrochloride, of (S) stereochemistry at the 2-position, as a white foam (80 mg, 37%, based on single isomer); a portion of this was subsequently crystallised as the (S) free base, m.p. 128°–130° C.:

Analysis %: Found: C, 67.9; H. 7.07; N, 11.69: $C_{20}H_{25}N_3O_3$ requires: C, 67.58; H, 7.09; N, 11.82.

Fractions containing the second eluted diastereoisomer were also combined and evaporated to give the title compound, of (R) stereochemistry at the 2-position, as a white solid (50 mg, 28%, based on single isomer) which was recrystallised from acetone, m.p. 156°–158° C., $|\alpha|_{589}^{25} + 93.8$ (c=1% in ethanol):

Analysis %: Found: C, 67.30; H, 7.07; N, 11.80; $C_{20}H_{25}N_3O_3$ requires: C, 67.58; H, 7.09; N, 11.82.

EXAMPLE 2

(R)-3-Quinuclidinyl (R and S)-3-hydroxy-2-phenyl-2-(1H-pyrazol-1-ylmethyl)-propanoate

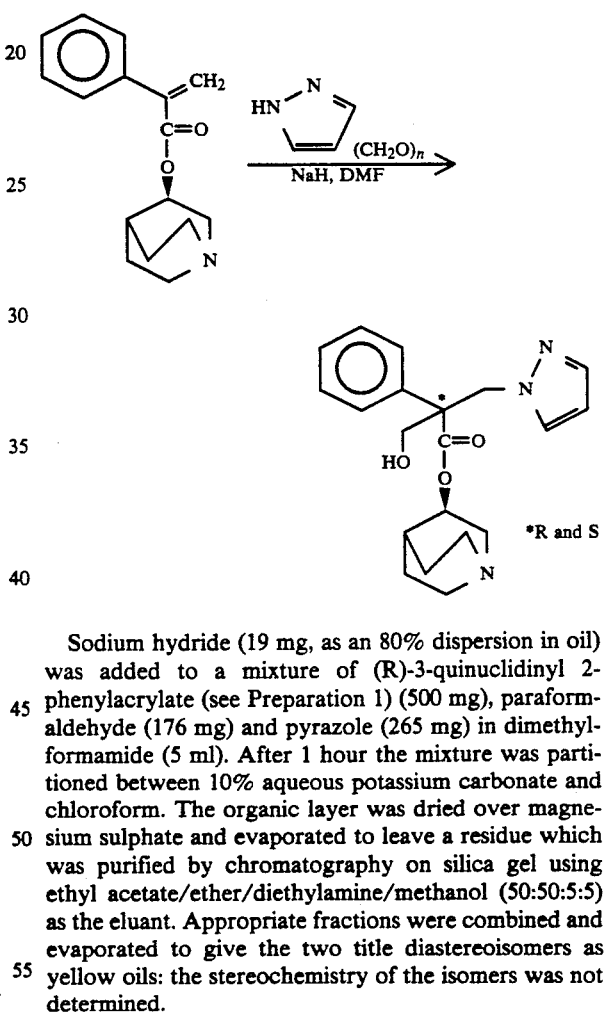

Sodium hydride (19 mg, as an 80% dispersion in oil) was added to a mixture of (R)-3-quinuclidinyl 2-phenylacrylate (see Preparation 1) (500 mg), paraformaldehyde (176 mg) and pyrazole (265 mg) in dimethylformamide (5 ml). After 1 hour the mixture was partitioned between 10% aqueous potassium carbonate and chloroform. The organic layer was dried over magnesium sulphate and evaporated to leave a residue which was purified by chromatography on silica gel using ethyl acetate/ether/diethylamine/methanol (50:50:5:5) as the eluant. Appropriate fractions were combined and evaporated to give the two title diastereoisomers as yellow oils: the stereochemistry of the isomers was not determined.

Diastereoisomer 1 (first eluted isomer) (120 mg, 35% $^1$H NMR (300 MHz, CDCl$_3$) δ=1.2–2.1 (m, 5H), 2.4–3.0 (m, 5H), 3.2 (m, 1H), 3.8–4.2 (m, 2H), 4.6–5.1 (m, 3H), 6.2 (s, 1H), 7.2–7.6 (m, 7H) ppm.

Mass spectrum: m/e (MH)$^+$=356

Diastereoisomer 2 (second eluted isomer) (100 mg, 29% $^1$H NMR (300 MHz, CDCl$_3$) δ=1.2–1.9 (m, 5H), 2.4–2.8 (m, 5H), 3.2 (m, 1H), 3.8–4.2 (m, 2H), 4.6 (d, 1H), 4.8 (m, 1H), 5.0 (d, 1H), 6.2 (s, 1H) 7.2–7.4 (m, 6H), 7.55 (s, 1H) ppm.

Mass spectrum: m/e (M/H)$^+$=356

EXAMPLES 3 TO 13

The following tabulated Examples of the general formula:

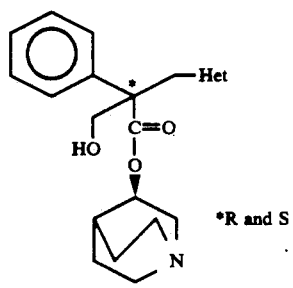

*R and S where obtained by similar methods to that described in Example 2 using (R)-3-quinuclidinyl 2-phenylacrylate (see Preparation 1) and the appropriate heterocycle. Individual experimental variations, and the absolute stereochemistry at position 2, where identified, is indicated in the Table. "Diastereoisomers 1 and 2" refer simply to the order of elution from the column and not to any stereochemistry.

| Example No. | H—Het | Experimental Variations | Analytical Data |
|---|---|---|---|
| 3 | H—N⟨triazole⟩ | Diastereomer 1 was treated with ethereal hydrogen chloride. | Diastereoisomer 1 - solid foam as a dihydrochloride.<br><br>Analysis %:-<br>Found: C, 53.63; H, 6.63; N, 12.00;<br>$C_{19}H_{24}N_4O_3$.2HCl.$\frac{1}{4}$EtOAc<br>requires: C, 53.28; H, 6.39; N, 11.84.<br>Diastereoisomer 2 - white solid, m.p. 127-130° C.<br>Analysis %: -<br>Found: C, 63.86; H, 6.75; N, 15.45;<br>$C_{19}H_{24}N_4O_3$<br>requires: C, 64.03; H, 6.78; N, 15.72. |
| 4 | HN⟨tetrazole⟩ | Reaction time 24 hours, chromatography solvent CHCl$_3$ plus 0 → 5% MeOH + 0 → 5% NH$_3$ (aq.) | Diastereoisomer 1, (S) stereochemistry - white solid, m.p. 184-186° C.<br><br>Analysis %:-<br>Found: C, 60.56; H, 6.41; N, 19.53;<br>$C_{18}H_{23}N_5O_3$<br>requires: C, 60.49; H, 6.49; N, 19.60.<br>Diastereoisomer 2, (R) stereochemistry - white solid, m.p. 171-173° C.<br>Analysis %:-<br>Found: C, 60.38; H, 6.44; N, 19.22;<br>$C_{18}H_{23}N_5O_3$<br>requires: C, 60.49; H, 6.49; N, 19.60. |
| 5<br>In this Example 1,2,3-triazolyl- and 1,2,5-triazolyl- products were obtained in approx. equal portions. | HN⟨triazole⟩ | Chromatography solvent - EtoAc/Et$_2$O/HNEt$_2$/MeOH (50:50:2.5:2.5); diastereoisomers 1 and 2 of the 1,2,5-triazole products were eluted first followed by diastereomers 1 and 2 of the 1,2,3-triazole product. | 1,2,5-triazoles<br>Diastereoisomer 1, (S) stereochemistry - white solid m.p. 132-133°C.<br>$^1$H-NMR(300MHz, CDCl$_3$)δ=1.2-1.7(m, 4H), 2.0(m, 1H), 2.6-2.8(m, 5H), 3.2(m, 1H), 4.1(m, 2H), 4.85(2, 1H), 5.15(d, 1H), 5.35(d, 1H), 7.2-7.4(m, 5H), 7.6(s, 2H)ppm.<br>Mass spectrum: m/e (M$^+$) = 356<br>Diastereoisomer 2, (R) stereochemistry - white solid m.p. 124-125° C.<br><br>$^1$H-NMR(300MHz, CDCl$_3$)δ=1.2-1.7(m, 4H), 2.0(m, 1H), 2.5-2.8(m, 5H), 3.15(m, 1H), 4.1(s, 2H), 4.9(m, 1H), 5.15(d, 1H), 5.3 (d, 1H), 7.2-7.4(m, 5H), 7.6(s, 1H)ppm.<br>Mass spectrum: m/e (M$^+$) = 356.<br>1,2,3-triazoles<br>Diastereoisomer 1 - yellow oil.<br>$^1$H-NMR(300MHz, CDCl$_3$)δ=1.2-1.7(m, 4H), 2.0(m, 1H), 2.4-2.8(m, 5H), 3.2(m,1H), |

-continued

| Example No. | H—Het | Experimental Variations | Analytical Data |
|---|---|---|---|
| | | | 4.1(m, 2H), 4.85(m, 3H), 5.25(d, 1H), 7.2–7.4(m, 5H), 7.6(s, 1H)ppm. Mass spectrum: m/e (M$^+$) = 356 Diastereoisomer 2 - yellow oil. $^1$H-NMR(300MHz, CDCl$_3$)δ=1.2–1.7(m, 4H), 2.0(m, 1H), 2.6–2.8(m, 5H), 3.15(m, 1H), 4.1(m, 2H), 4.8(m, 3H), 5.25(d, 1H), 7.1–7.4(m, 5H), 7.55(s, 1H)ppm. Mass spectrum: m/e (M$^+$) = 356 |
| 6 | HN–N=N–Cl (imidazole-type with Cl) | Chromatography solvent EtOAc/Et$_2$O/HNEt$_2$/MeOH (50:50:5:5) | Diastereoisomer 1 - (S) stereochemistry, white solid, m.p. 118–120° C. |
| | Prepared as described in Khim. Geterotsisikl. Soedin, 1701, 12, 1970. | | Analysis %:- Found: C, 58.17; H, 5.87; N, 14.40. C$_{19}$H$_{23}$ClN$_4$O$_3$ requires: C, 58.38; H, 5.93; N, 14.33. Diastereoisomer 2 - (R) stereochemistry, white solid, m.p. 110–113° C. Analysis %:- Found: C, 58.48; H, 5.91; N, 14.58; C$_{19}$H$_{23}$ClN$_4$O$_3$ requires: C, 58.38; H, 5.93; N, 14.33. |
| 7 | HN–N (Me-substituted imidazole) | Chromatography solvent- EtOAc/Et$_2$O/HNEt$_2$/ MeOH (50:50:5:5) | Diastereoisomer 1 - yellow foam. |
| | | | $^1$H-NMR(300MHz, CDCl$_3$)δ=1.2–1.8 (m, 4H), 1.9(s, 3H), 2.05(s, 1H), 2.6– 2.9(m, 5H), 3.25(m, 1H), 4.0(d, 1H), 4.25(d, 1H), 4.35(d, 1H)4.7(d, 1H), 4.95(m, 1H), 6.55(s, 1H), 6.8(s, 1H), 7.0–7.4(m, 5H)ppm. Mass spectrum: m/e (MH$^+$) = 370 Diastereoisomer 2 - yellow foam. $^1$H-NMR(300MHz, CDCl$_3$)δ=1.2–1.8(m, 4H), 1.9(s, 3H), 1.95(s,1H), 2.6–2.9 (m, 5H), 3.2(m, 1H), 4.0(d, 1H), 4.25 (d,1H), 4.35(d, 1H), 4.75(d, 1H), 5.0 (m, 1H), 6.45(s, 1H), 6.8(s, 1H), 7.0 (m, 2H), 7.35(m, 3H)ppm. Mass spectrum: m/e (MH$^+$) = 370. |
| 8 | HN–N (4-Me imidazole) | Chromatography solvent CHCl$_3$ + 0 → 5%, MeOH and 0 → ½% NH$_3$ (aq.) | Diastereoisomer 1, a mixture of the 4- and 5-methyl isomers, as a white foam. |
| | | | $^1$H-NMR(300MHz, CDCl$_3$)δ=1.2–2.2(m, 8H), 2.4–3.0(m, 5H), 3.2(m, 1H), 3.8–5.0(m, 5H), 6.0–7.4(m, 7H)ppm. Mass spectrum: m/e (MH$^+$) = 370. Diastereoisomer 2, a mixture of the 4- and 5-methyl isomers, as a white foam. $^1$H-NMR(300MHz, CDCl$_3$)δ=1.2–2.2(m, 8H), 2.4–2.8(m, 5H), 3.2(m, 1H), 3.8–4.8(m, 5H), 6.0–7.4(m, 7H)ppm. Mass spectrum: m/e (MH$^+$) = 370. |
| 9 | *HN–N=N–Br (Me, Br substituted triazole) | — | Diastereoisomer 1 - (S) stereochemistry as a white solid, m.p. 180° C. |
| | *reacting centre. 3(5)-Bromo-5(3)- methyl-1,2,4- triazole was | | Analysis %:- Found: C, 53.28; H, 5.60; N, 12.17 C$_{20}$H$_{25}$BrN$_4$O$_3$ requires: C, 53.46; H, 5.60; N, 12.47. |

-continued

| Example No. | H—Het | Experimental Variations | Analytical Data |
|---|---|---|---|
|  | prepared as described in Chem. Ber., 2250, 100, 1967. |  | Diastereoisomer 2 (R) stereochemistry as a white solid, m.p. 181° C.<br>Analysis %:-<br>Found: C, 52.99; H, 5.71; N, 12.05;<br>$C_{20}H_{25}BrN_4O_3$<br>requires: C, 53.46; H, 5.60; N, 12.47. |
| 10 | [structure: triazole with Et group, *HN, N, N, Br] | Diastereoisomer 2 crystallised directly from ether/ethyl acetate/HNEt$_2$/MeOH (50:50:5:5). | Diastereoisomer 2 - white solid, m.p. 180–189° C. |
|  | *reacting centre.<br>3(5)-Bromo-5(3)-ethyl-1,2,4-triazole was prepared from 3(5)-ethyl-1,2,4-triazole (see J. Amer. Chem. Soc., 1985, 71, 1949) by the method described in Chem. Ber., 2250, 100, 1967. |  | Analysis %:<br>Found: C, 54.70; H, 5.87; N, 12.03,<br>$C_{21}H_{27}N_4O_3Br$<br>requires: C, 54.43; H, 5.87; N, 12.09. |
| 11 | [structure: triazole with CH$_3$-CH$_2$-CH$_2$- group, *HN, N, N, Br] | — | Diastereoisomer 1 - yellow oil. |
|  | *reacting centre<br>3(5)-Bromo-5(3)-propyl-1,2,4-triazole was prepared from 3(5)-propyl-1,2,4-triazole (see Chem. Ber., 2033, 101, 1968) by the method described in Chem. Ber., 2250, 100, 1967. |  | $^1$H-NMR(300MHz, CDCl$_3$)δ=1.2–1.8(m, 9H), 1.9–2.2(m, 3H), 2.7–2.9(m, 5H), 3.2 (m, 1H); 3.4(BrS, 1H), 4.1–4.4(m, 2H), 4.45(d, 1H), 4.85(d, 1H), 4.9(m, 1H), 7.1–7.4(m, 5H)ppm.<br>Mass spectrum: m/e (MH$^+$) = 477.<br>Diastereoisomer 2 - white solid.<br>$^1$HNMR(300MHz, CDCl$_3$)δ=1.2–2.2(m, 12H), 2.6–2.8(m, 5H), 3.2(m, 1H), 4.2–4.35(m, 2H), 4.4(d, 1H), 4.8(d, 1H), 4.9(m, 1H), 7–7.4(m, 5H)ppm.<br>Mass spectrum: m/e (MH$^+$) = 477. |
| 12 | [structure: triazole with Me$_2$CH group, *HN, N, N, Br] | — | Diastereoisomer 1 - yellow foam. |
|  | *reacting centre<br>3(5)-Bromo-5(3)-isopropyl-1,2,4-triazole was prepared from 3(5)-isopropyl-1,2,4-triazole (see Chem. Ber., 2033, 101, 1968) by the method described in Chem. Ber., 2250, 100, 1967. |  | $^1$H-NMR(300MHz, CDCl$_3$)δ=0.9(d, 3H), 1.1 (d, 3H), 1.1–1.8(m, 4H), 2.2–2.8(m, 6H), 3.2(m, 1H), 4.2(d, 1H), 4.35(d, 1H), 4.45(d, 1H), 4.8(d, 1H), 4.9(m, 1H), 7.1 (m, 2H), 7.35(m, 3H)ppm.<br>Mass spectrum: m/e (MH$^+$) = 478<br>Diastereoisomer 2 - white solid m.p. 173–174° C.<br>Analysis %:<br>Found: C, 55.45; H, 6.06; N, 11.36<br>$C_{22}H_{29}N_4O_3Br$<br>requires: C, 55.35; H, 6.12; N, 11.74. |

-continued

| Example No. | H—Het | Experimental Variations | Analytical Data |
|---|---|---|---|
| 13 | (structure shown) | — | Diastereoisomer 1 - yellow oil |
| | *reacting centre<br>3(5)-Bromo-5(3)-isobutyl-1,2,4-triazole was prepared from 3(5)-isobutyl-1,2,4-triazole (see EP-A-122693) by the method described in Chem. Ber., 2250. 100, 1967. | | $^1$H-NMR(300MHz, CDCl$_3$)δ=0.8(m, 6H), 1.2–1.4(m, 2H), 1.4–1.8(m, 3H), 1.8–2.2 (m, 6H), 3.2(m, 1H), 4.1(d, 1H), 4.3(d, 1H), 4.4(d, 1H), 4.8(d, 1H), 4.9(m, 1H), 7.1(m, 2H), 7.3(m, 3H)ppm.<br>Diastereoisomer 2 - yellow oil<br>$^1$H-NMR(300MHz, CDCl$_3$)δ=0.8(m, 6H), 1.1–2.2(m, 5H), 2.6(m, 1H), 2.7(m, 5H), 3.2 (m, 1H), 4.2–4.5(m, 3H), 4.85(d, 1H), 4.9 (m, 1H), 7.1(m, 2H), 7.3(m, 3H)ppm. |

EXAMPLE 14

(R)-3-Quinclidinyl (R and S)-2-(2-azido-1H-imidazol-1-ylmethyl)-3-hydroxy-2-phenylpropanoate

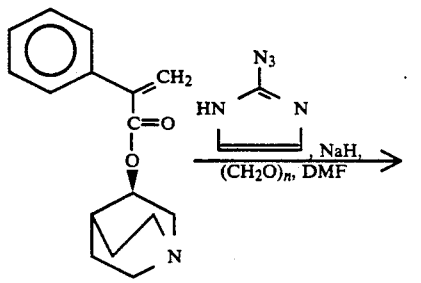

The title compounds, the stereochemistry of which at the 2-position was not characterised, were prepared by a similar method to that described in Example 2 but using 2-azidoimidazole (prepared as described in Tet. Lett., 1523, 18, 1975).

Diastereoisomer 1 (higher Rf by tlc) as a white solid (60%) m.p. 136° (dec).

$^1$H-NMR (300 MHz, CDCl$_3$) δ=1.2–2.1 (m, 5H), 2.2–3.0 (m, 5H), 3.2 (m, 1H), 4.0 (d, 1H), 4.25 (d, 1H), 4.3 (d, 1H), 4.55 (d, 1H), 4.95 (m, 1H), 6.2 (s, 1H), 6.8 (s, 1H), 7.1 (m, 2H), 7.35 (m, 3H) ppm.

Mass spectrum: m/e (M+)=396.

Diastereoisomer 2 (lower Rf by tlc) as a brown oil (67%)

$^1$H-NMR (300 MHz, CDCl$_3$) δ=1.2–18 (m, 4H), 1.95 (s, 1H), 2.7 (m, 5H), 3.2 (m, 1H), 4.0 (d, 1H), 4.2–4.4 (m, 2H), 4.5 (d, 1H), 4.95 (m, 1H), 6.2 (s, 1H), 6.7 (s, 1H), 7.05 (m, 1H), 7.35 (m, 3H) ppm.

Mass spectrum: m/e (M-N$_2^+$)=368

EXAMPLE 15

(R)-3-Quinclidinyl (R and S)-2-(2-amino-1H-imidazol-1-ylmethyl)-3-hydroxy-2-phenylpropanoate

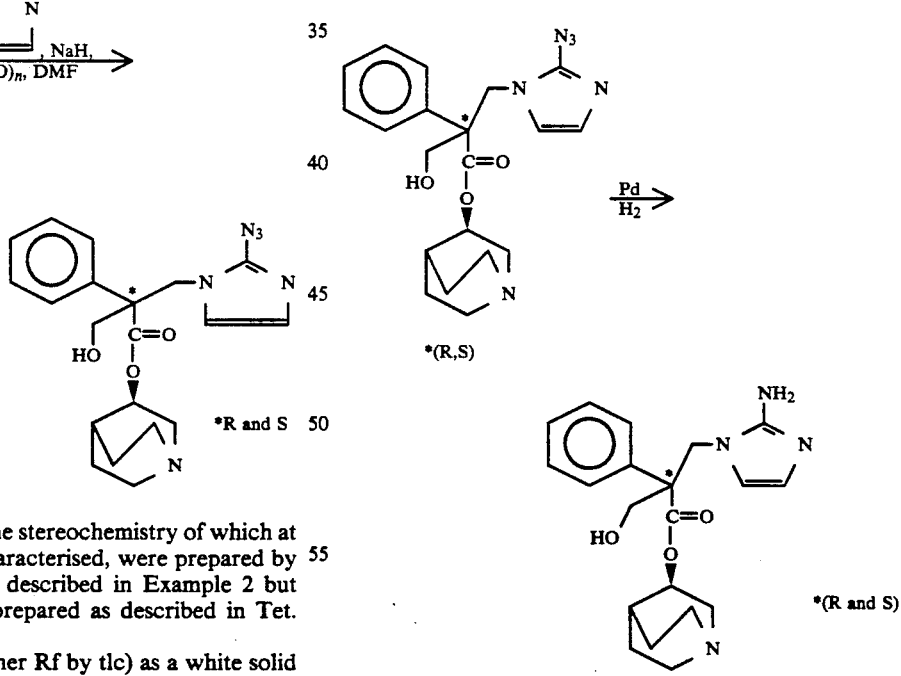

Diastereomers 1 and 2 of (R)-3-quinuclidinyl (R and S)-2-(2-azido-1H-imidazol-1-ylmethyl)-3-hydroxy-2-phenylpropanoate (see Example 14) (400 mg) were separately hydrogenated in ethanol (15 ml) containing 10% palladium-on-carbon (40 mg) at room temperature in an atmosphere of hydrogen [344.7 kPa, (50 psi)]. Filtration and evaporation gave the two title compounds as amorphous white solids; the stereochemistry at the 2-positions of these diastereomers was not determined.

Diastereoisomer 1 (higher Rf by tlc) (350 mg, 93.6%).
$^1$H-NMR (300 MHz, CDCl$_3$) δ=1.2–18 (m, 4H), 2.0 (m, 1H), 2.4–2.8 (m, 5H), 3.2 (m, 1H), 4.0 (d, 1H), 4.2 (m, 2H), 4.7 (d, 1H), 4.9 (m, 1H), 5.8 (s, 1H), 6.4 (s, 1H), 7.0–7.4 (m, 5H) ppm.
Mass spectrum: m/e (M$^+$)=370
Diastereoisomer 2 (lower Rf by tlc) (310 mg, 84%)
$^1$H-NMR (300 MHz, CDCl$_3$) δ=1.2–2.1 (m, 5H), 2.6–2.8 (m, 5H), 3.1 (m, 1H), 4.0–5.0 (m, 5H), 5.8 (s, 1H), 6.4 (s, 1H), 7.1–7.4 (m, 5H) ppm.
Mass spectrum m/e (M$^+$)=370

EXAMPLE 16

(R)-3-Quinclidinyl
(R)-3-hydroxy-2-(5-methyl-1H-1,2,4-triazol-1-ylmethyl)-2-phenylpropanoate

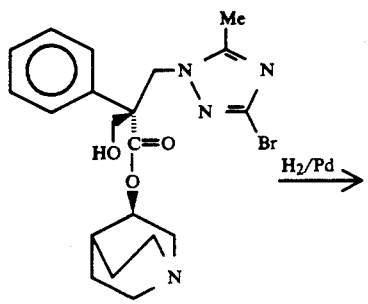

A solution of (R)-3-quinuclidinyl (R)-2-(3-bromo-5-methyl-1H-1,2,4-triazol-1-ylmethyl)-3-hydroxy-2-phenylpropanoate (see Example 9) (1.2 g) in ethanol (25 ml) containing 10% palladium-on-carbon (120 mg) was stirred for 16 hours under an atmosphere of hydrogen [344.7 kPa (50 psi)] at room temperature, filtered and evaporated to leave a residue that was partitioned between 10% aqueous potassium carbonate and ethyl acetate. The organic layer was dried over magnesium sulphate and the residue, after evaporation, recrystallised from ethyl acetate to leave the title compound as a white solid (0.72 g, 73%, m.p. 194°–196° C.

Analysis %: Found: C, 64.76; H, 7.11; N, 14.77; C$_{20}$H$_{26}$N$_4$O$_3$ requires: C, 64.85; H, 7.07; N, 15.12.

EXAMPLES 17 TO 20

The following tabulated Examples of the general formula:

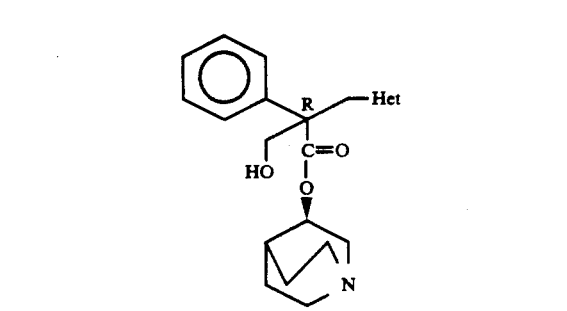

were obtained by similar methods to that described in Example 16 by hydrogenation of diastereoisomer 2 of the appropriate bromo-containing quinuclidinyl starting material. Individual experimental variations are indicated in the Table, as are the details of the staring materials. The products by analogy with Example 16 have (R) stereochemistry.

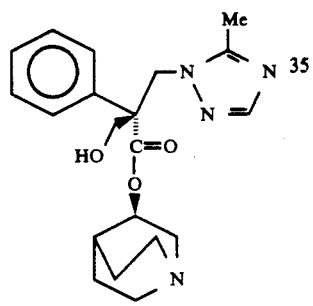

| Example No. | Het | Experimental Variation | Analytical Data |
|---|---|---|---|
| 17 | ![structure with Me]  -N-N=N with Me ethyl group  (See Example 10) | — | Yellow foam  $^1$H-NMR(300MHz, CDCl$_3$)δ=1.0(t, 3H), 1.6–2.2(m, 7H), 3.2–3.4(m, 5H), 3.7(m, 1H), 4.2(d, 1H), 4.4(m, 2H), 4.8(d, 1H), 5.2(m, 1H), 6.9(m, 2H), 7.3(m, 3H), 7.8 (s, 1H)ppm.  Mass spectrum: m/e (MH$^+$) = 385. |
| 18 | ![structure with Me] -N-N=N with Me ethyl group  (See Example 11) | Purified by chromatography on silica using CHCl$_3$/MeOH (95:5) as eluant. | White solid.  $^1$H-NMR(300MHz, CDCl$_3$)δ=0.9(t, 3H), |

-continued

| Example No. | Het | Experimental Variation | Analytical Data |
|---|---|---|---|
| | | | 0.95(m, 2H), 1.2–2.2(7H), 2.9(m, 5H), 3.3(m, 1H), 3.4(B.S., 1H), 4.2(d, 1H), 4.3(d, 1H), 4.4(d, 1H), 4.8(d, 1H), 5.0 (m, 1H), 7.0(m, 2H), 7.3(m, 3H), 7.8(s, 1H)ppm.<br>Mass spectrum: m/e (MH+) = 399. |
| 19 | Me₂CH-[1,2,4-triazolyl]<br>(See Example 12) | Purified by chromatography on silica using CHCl₃ + MeOH 2 → 5% as eluant. | White solid. m.p. 182–183° C.<br>¹H-NMR(300MHz, CDCl₃)δ=0.9(t, 3H), 1.2(t, 3H), 1.25–2.0(5H), 2.5(m, 1H), 2.75(m, 5H), 3.2(m, 1H), 4.25(m, 2H), 4.5(d, 1H), 4.9(m, 2H), 7.1(m, 2H), 7.3 (m, 3H), 7.8(s, 1H)ppm.<br>Mass spectrum: m/e (MH+) = 399. |
| 20 | Me₂CHCH₂-[1,2,4-triazolyl]<br>(See Example 13) | Purified by chromatography on silica using EtOAc/Et₂O/HNEt₂/MeOH (50:50:2.5:2.5) as eluant. | White solid. m.p. 104–106° C.<br>¹H-NMR(300MHz, CDCl₃)δ=0.8(d, 3H), 0.9(d, 3H), 1.2–2.0(m, 5H), 2.6(m, 1H), 2.7(m, 5H), 3.25(m, 1H), 4.2(m, 2H), 4.4 (d, 1H), 4.9(m, 2H), 7.15(m, 2H), 7.35 (m, 3H), 7.9(s, 1H)ppm.<br>Mass spectrum: m/e (MH+) = 413. |

EXAMPLE 21

(R)-3-Quinclidinyl (R and S)-3-hydroxy-2-phenyl-2-(pyrazin-2-ylmethyl)propanoate

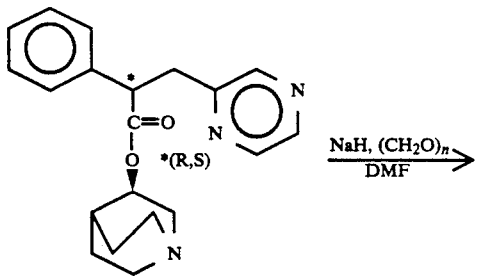

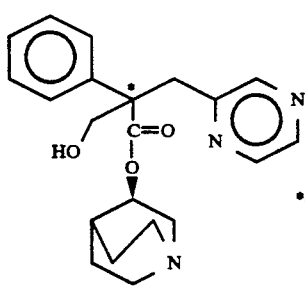

To a mixture of (R)-3-quinuclidinyl (R,S)-2-phenyl-3-(pyrazin-2-yl)propanoate (see Preparation 5) (300 mg) and paraformaldehyde (60 mg) in dimethylformamide (4 ml) was added sodium hydride (29 mg as an 80% dispersion in oil). The mixture was stirred for 1 hour at room temperature then partitioned between ethyl acetate and 10% aqueous potassium carbonate. The organic layer was dried over magnesium sulphate then evaporated to give a residue which as purified by chromatography on silica gel by gradient elution using chloroform plus methanol (0→10%) and aqueous ammonia (0→1%). Appropriate fractions were combined and evaporated to give the two title diastereomers, of undefined stereochemistry at the 2-positions, as yellow oils.

Diastereoisomer 1 (higher Rf by tlc) (65 mg, 40%)
¹H-NMR (300 MHz, CDCl₃) δ=1.2–1.7 (m, 4H), 1.95 (m, 1H), 2.4–2.8 (m, 5H), 3.15 (m, 2H), 3.5 (d, 2H), 3.75 (d, 2H), 4.1 (m, 2H), 4.95 (m, 2H), 7.2–7.4 (m, 5H), 8.4 (s, 1H), 8.5 (d, 1H) ppm.
Mass spectrum: m/e (MH+)=368

Diastereoisomer 2(lower Rf by tlc) (40 mg, 24.5%)
¹H-NMR (300 MHz, CDCl₃) δ=1.2–1.8 (m, 4H), 1.95 (s, 1H), 2.4–2.8 (m, 5H), 3.2 (m, 1H), 3.5 (d, 1H), 3.8 (d, 1H), 4.1 (m, 2H), 4.8 (m, 1H), 7.3 (m, 5H), 8.4 (s, 1H), 7.5 (s, 1H).
Mass spectrum: m/e (MH+)=368

EXAMPLES 22 TO 25

The following tabulated Examples of general formula:

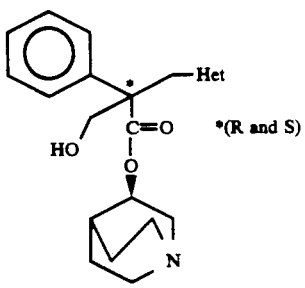

*(R and S)

were obtained by similar methods to that described in Example 21 by hydroxymethylation of the appropriate quinuclidinyl starting material. Individual experimental variations are indicated in the Table, as are the Preparation numbers of the starting materials. Diastereoisomers 1 and 2 refer simply to the order of elution from the column and not to any stereochemistry.

| Example No. | H—Het | Experimental Variations | Analytical Data |
|---|---|---|---|
| 22 | N (See preparation 8) | $(CH_2O)_n$ and NaH prestirred in DMF for 15 minutes prior to addition of substrate<br><br>Chromatography solvent EtOAc/Et$_2$O/HNE$_t$/MeOH (50:50:2:2) | Diastereoisomer 1 - yellow oil.<br><br>$^1$H-NMR(300MHz, CDCl$_3$)$\delta$ = 1.2–1.7(m, 4H), 1.95(m, 1H), 2.4–2.8(m, 5H), 3.1(m, 1H), 3.4(d, 1H), 3.7(d, 1H), 4.15(m, 2H), 4.8 (m, 1H), 7.1(m, 2H), 7.35(m, 3H), 8.6(d, 2H), 9.1(s, 2H)ppm.<br>Mass spectrum: m/e (MH)$^+$ = 368.<br>Diastereoisomer 2 - white solid m.p. 124–125° C.<br>Analysis %:-<br>Found: C, 68.24; H, 6.56; N, 11.06;<br>C$_{21}$H$_{25}$N$_3$O$_3$<br>requires: C, 68.64; H, 6.86; N, 11.44. |
| 23 | N (see Preparation 10) | — | Diastereoisomer 1 - yellow oil.<br><br>$^1$H-NMR(300MHz, CDCl$_3$)$\delta$ = 1.2–1.7(m, 4H), 1.95(m, 1H), 2.4–2.8(m, 5H), 3.15 (m, 1H), 3.5(d, 1H), 3.75(d, 1H), 4.1(m, 2H), 4.8(m, 1H), 7.0–7.6(m, 8H), 8.5(d, 1H)ppm.<br>Mass spectrum: m/e (MH$^+$) = 367.<br>Diastereoisomer 2 - yellow oil.<br>Analysis %:-<br>Found: C, 63.60; H, 6.54; N, 6.43;<br>C$_{22}$H$_{26}$N$_2$O$_3$·$\frac{1}{2}$CHCl$_3$<br>requires: C, 63.41; H, 6.26; N, 6.57. |
| 24 | N (See Preparation 11) | — | Diastereoisomer 1 - yellow oil.<br><br>$^1$H-NMR(300MHz, CDCl$_3$)$\delta$ = 1.2–2.4(m, 5H), 2.8–3.2(m, 5H), 3.2–3.6(m, 3H), 4.0(d, 1H), 4.2(d, 1H), 5.1(m, 1H), 7.0–7.4(m, 7H), 8.2(s, 1H), 8.4(s, 1H)ppm.<br>Mass spectrum: m/e (MH$^+$) = 367.<br>Diastereoisomer 2 - yellow oil.<br>$^1$H-NMR(300MHz, CDCl$_3$)$\delta$ = 1.2–2.2(m, 5H), 2.6–2.9(m, 5H), 3.3(m, 1H), 3.5(m, 2H), 3.9(d, 1H), 4.2(d, 1H), 4.9(m, 1H), 7.0–7.4(m, 7H), 8.2(s, 1H), 8.5(d, 1H)ppm.<br>Mass spectrum: m/e (MH$^+$) = 367. |
| 25 | N (See Preparation 12) | Chromatography solvent - EtOAc/Et$_2$/MeOH (50:50:2.5:2.5) | Diastereoisomer 1 - yellow oil.<br><br>$^1$H-NMR(300MHz, CDCl$_3$)$\delta$ = 1.2–2.2(m, 5H), 2.6–2.9(m, 5H), 3.2(m, 1H), 3.5(m, 2H), 3.9(d, 1H), 4.1(d, 1H), 4.9(m, 1H), 6.9 |

| Example No. | H—Het | Experimental Variations | Analytical Data |
|---|---|---|---|
| | | | (d, 1H), 7.2–7.5(m, 6H), 8.4(m, 2H)ppm. Mass spectrum: m/e (MH$^+$) = 367. Diastereoisomer 2 - yellow oil. $^1$H-NMR(300MHz, CDCl$_3$)δ=1.2–2.2(m, 5H), 2.6–3.0(m, 5H), 3.2(m, 1H), 3.4(d, 1H), 3.5(d, 1H), 3.9(d, 1H), 4.2(d, 1H), 4.9 (m, 1H), 6.9(d, 1H), 7.2(d, 1H), 7.3(m, 5H), 8.4(m, 2H)ppm. Mass spectrum: m/e (MH$^+$) = 367. |

EXAMPLE 26

(R)-3-Quinuclidinyl (R and S)-3-hydroxy-2-(1H-methylpyrazol-5-ylmethyl)-2-phenylpropanoate

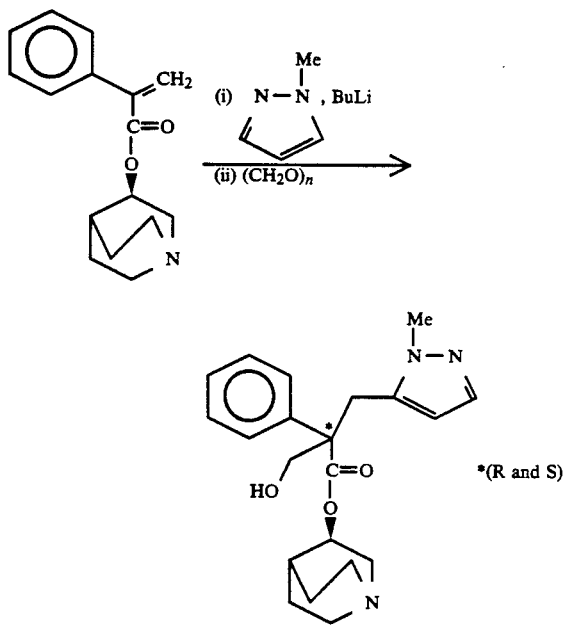

N-butyllithium (2.1 ml of a 1.6 molar solution in hexane) was added to N-methylpyrazole (284 mg) in tetrahydrofuran (10 ml) at −78° C. After 2 hours (R)-3-quinuclidinyl 2-phenylacrylate (see Preparation 1) (771 mg) in tetrahydrofuran (5 ml) was added and the mixture stirred for ½ at −78° C., then allowed to warm slowly to 0° C., when paraformaldehyde (180 mg) was added. After 1½ hours the mixture was partitioned between 10% aqueous potassium carbonate and ethyl acetate, the organic layer dried (magnesium sulphate) and evaporated. The residue was purified by chromatography on silica gel by gradient elution using ethyl acetate/ether/diethylamine/methanol (50:50:2.3:2.5→50:50:5:5) as eluant. Appropriate fractions were combined and evaporated to give the two title compounds, of undefined stereochemistry at the 2-positions, as white solids.

Diastereoisomer 1 (higher Rf by tlc) (100 mg, 18%) m.p. 130°–131° C.

Analysis %:
Found: C, 66.87; H, 7.26; N, 11.10. C$_{21}$H$_{27}$N$_3$O$_3$.½ H$_2$O requires: C, 66.64; H, 7.45; N, 11.10.

Diastereoisomer 2 (lower Rf by tlc) (120 mg, 21%) m.p. 124°–126° C.

Analysis %: Found: C, 68.32; H, 7.40; N, 11.80; C$_{21}$H$_{27}$N$_3$O$_3$ requires: C, 68.27; H, 7.36; N, 11.37.

EXAMPLE 27

(R)-3-Quinuclidinyl (R and S)-3-hydroxy-2-(1-methylimidazol-2-ylmethyl)-2-phenyl propanoate

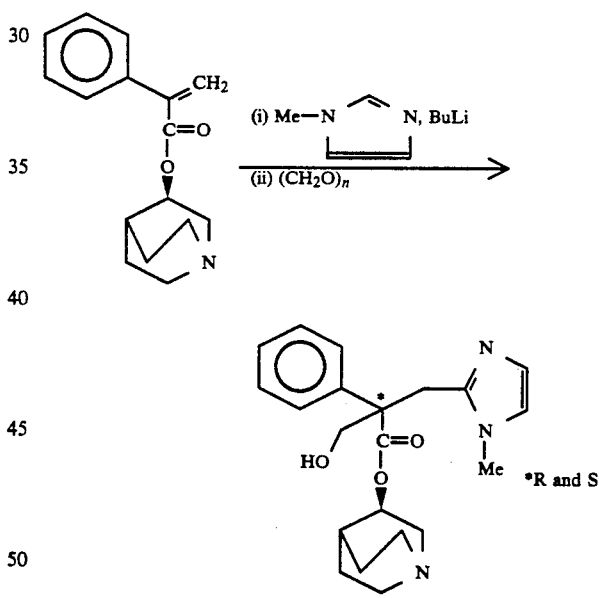

The title compounds of undefined stereochemistry, were obtained, as yellow oils, by a similar method to that described in Example 26 using N-methylimidazole in place of N-methylpyrazole.

Diastereoisomer 1 (higher Rf by tlc) (21%)
$^1$H-NMR (300 MHz, CDCl$_3$) δ=1.2–1.8 (m, 4H); 2.0 (s, 1H). 2.4–28 (m, 5H), 3.2 (m, 2H), 3.4 (s, 3H). 3.6 (d, 2H). 4.2 (d, 2H), 4.4 (d, 2H), 4.9 (m, 1H), 6.75 (s, 1H), 6.95 (s, 1H), 7.2–7.4 (m, 5H) ppm.
Mass spectrum: m/e (MH$^+$)=370.

Diastereoisomer 2 (lower Rf by tlc) (43%)
$^1$H-NMR (300 MHz, CDCl$_3$) δ=1.2–1.8 (m, 4H); 1.95 (s, 1H). 2.6–2.9 (m, 5H), 3.2 (m, 2H), 3.4 (s, 3H), 3.6 (d, 2H), 4.25 (d, 1H), 4.4 (d, 1H), 4.85 (m, 1H), 6.7 (s, 1H), 6.95 (s, 1H), 7.2–7.5 (m, 5H) ppm.
Mass spectrum: m/e (MH$^+$)=370.

EXAMPLE 28

(R)-3-Quinuclidinyl (R and S)-3-hydroxy-2-(1H-methyl-1,2,3-triazol-5-ylmethyl)-2-phenylpropanoate

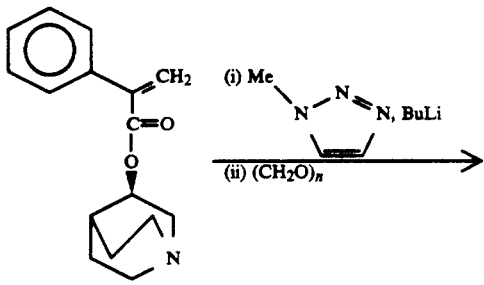

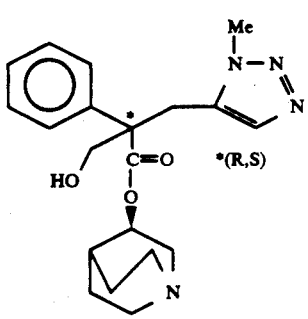

The title compounds, of undefined stereochemistry were obtained by a similar method to that described in Example 26 using N-methyl-1,2,3-triazole (prepared as described in Bull. Soc. Chim. France, 2998, 1967) in place of N-methylpyrazole.

Diastereoisomer 1 (higher Rf by tlc) as a white solid (27%) m.p. 200°-205° C.

$^1$H-NMR (300 MHz, CDCl$_3$) δ=1.0-1.8 (m, 4H), 2.05 (m, 1H), 2.4-3.0 (m, 5H), 3.2 (m, 1H), 3.4 (d, 1H), 3.6 (d, 1H), 3.65 (s, 3H), 3.9 (d, 1H), 4.25 (d, 1H), 4.95 (m, 1H), 7.05 (s, 1H), 7.15 (m, 2H), 7.4 (m, 3H) ppm.

Mass spectrum: m/e (M+)=370

Diastereoisomer 2 (lower Rf by tlc) as a yellow foam (29%)

$^1$H-NMR (300 MHz, CDCl$_3$) δ=1.0-1.8 (m, 4H), 1.95 (m, 1H), 2.6-3.0 (m, 5H), 3.2 (m, 1H), 3.4 (d, 1H), 3.6 (m, 2H), 3.9 (d, 1H), 4.3 (d, 1H), 5.0 (m, 1H), 6.95 (s, 1H), 7.05 (m, 2H), 7.3 (m, 3H) ppm.

Mass spectrum: m/e (M+)=370

EXAMPLE 29

(R)-3-Quinuclidinyl (R and S)-2-hydroxymethyl-4-(1-methylimidazol-2-yl)-2-phenylbutanoate

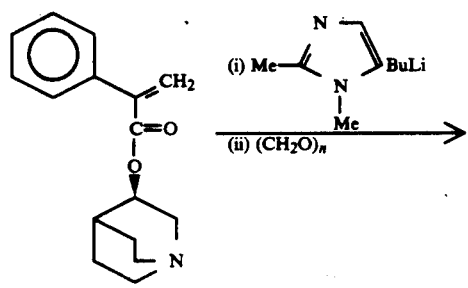

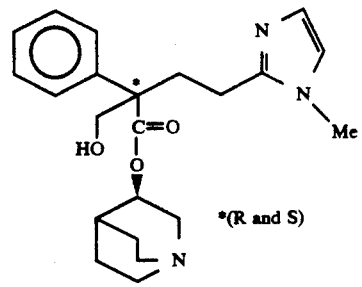

N-Butyllithium (13.6 ml of a 1.6 Molar solution in hexane) was added to 1,2-dimethylimidazole (2.11 g) in tetrahydrofuran (80 ml) at −78° C. After 1 hour the mixture was warmed to −15° C., stirred for ¼ hour and re-cooled to −78° C. when (R)-3-quinuclidinyl 2-phenylacrylate (see Preparation 1) (4.74 g) in tetrahydrofuran (40 ml) was added. After ¼ hour paraformaldehyde (1.2 g) was added and the mixture was slowly allowed to reach room temperature, stirred for 1 hour and partitioned between 10% aqueous sodium carbonate and ethyl acetate. The organic layer was dried over magnesium sulphate and evaporated to give a residue which was purified by chromatography on silica gel using ethyl acetate/ether/diethylamine/methanol (50:50:5.5) as the eluant. Appropriate fractions were combined and evaporated to give the two title compounds, with the C$_2$ stereochemistry indicated, as white solids.

Diastereoisomer 1 (higher RF by tlc), (R) stereochemistry (0.3 g, 8.4% based on single isomer), m.p. 186°-187° C.

Analysis %: Found: C, 68.18; H, 7.44; N, 10.76; C$_{22}$H$_{29}$N$_3$O$_3$ requires: C, 68.90; H, 7.62; N, 10.96.

Diastereoisomer 2 (lower Rf by tlc), (S) stereochemistry (250 mg, 7.1% based on single isomer), m.p. 197°-199° C.

Analysis %: Found: C, 69.07; H, 7.47; N, 10.84; C$_{22}$H$_{29}$N$_3$O$_3$ requires: C, 68.90; H, 7.62; N, 10.96.

EXAMPLES 30 TO 34

The following tabulated examples of the general formula:

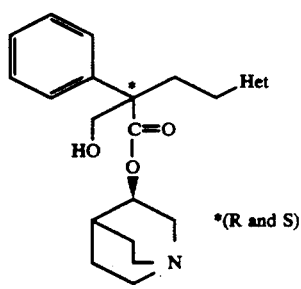

were obtained by similar methods to that described in Example 29 using (R)-3-quinuclidinyl 2-phenylacrylate and an appropriate anion (generated from the methylheterocycle of the formula CH$_3$-Het and base indicated). Individual experimental variations are as indicated in the tanle, diastereoisomers 1 and 2 merely refer to their relative positioning on tlc.

| Example No. | Het, base | Experimental Variations | Analytical Data |
|---|---|---|---|
| 30 | 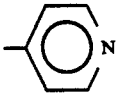<br>n-butyllithium | Anion generation totally at −78° C. [i.e. without warming to −15° C.] | Diastereoisomer 1 - white solid, m.p. 163–165° C.<br><br>Analysis %:-<br>Found: C, 71.77; H, 7.44; N, 7.12<br>$C_{23}H_{28}N_2O_3 \cdot \frac{1}{2}H_2O$<br>requires: C, 71.75; H, 7.46; N, 7.28.<br>Diastereoisomer 2 - white solid, m.p. 125–127° C.<br>Analysis %:-<br>Found: C, 72.51; H, 7.39; N, 7.3<br>$C_{23}H_{28}N_2O_3$<br>requires: C, 72.60; H, 7.42; N, 7.36. |
| 31 | 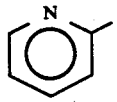<br>n-butyllithium | Anion generation totally at −78° C.; chromatography solvent: $CHCl_3$ plus 0 → 5% MeOH plus 0 → 0.5% $NH_3$ (aq). | Diastereoisomer 1 - white solid, m.p. 130–132° C.<br><br>$^1$H-NMR(300MHz, $CDCl_3$)δ=1.2–1.4(m, 2H), 1.5–1.8(m, 3H), 2.0(s, 1H), 2.5–3.0(m, 8H), 3.2(m, 1H), 4.1(d, 1H), 4.35(d, 1H), 4.9(m, 1H), 7.1(m, 2H), 7.2–7.4(m, 5H), 7.6(m, 1H), 8.5(d, 1H)ppm.<br>Mass spectrum: m/e (MH$^+$) = 381<br>Diastereoisomer 2 - white solid, m.p. 163–165° C.<br>$^1$H-NMR(300MHz, $CDCl_3$)δ=1.2–1.4(m, 1H), 1.4–1.8(m, 3H), 1.95(s, 1H), 2.5–2.9(m, 9H), 3.2(m, 1H), 4.1(d, 1H), 4.35(d, 1H), 4.85(m, 1H), 7.15(m, 2H), 7.2–7.4 (m, 5H), 7.6(m, 1H), 8.5(d, 1H)ppm.<br>Mass spectrum: m/e (MH$^+$) = 381 |
| 32 | 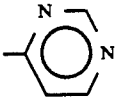<br>lithium diisopropylamide | Anion generation totally at −78° C.; chromatography solvent; $EtOAc/Et_2O/Et_2NH/MeOH$ (50:50:2.5:2.5) | Diastereoisomer 1 - white solid, m.p. 149–151° C.<br><br><br>Analysis %:<br>Found: C, 69.22; H, 7.25; N, 10.95<br>$C_{22}H_{27}N_3O_3$<br>requires: C, 69.27; H, 7.14; N, 11.02<br>Diastereoisomer 2 - white solid, m.p. 128–129° C.<br>Analysis %:<br>Found: C, 69.22; H, 7.30; N, 10.76<br>$C_{22}H_{27}N_3O_3$<br>requires: C, 69.27; H, 7.14; N, 11.02 |
| 33 | 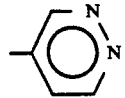<br>lithium diisopropylamide | Anion generation totally at −78° C.; chromatography solvent: $EtOAc/Et_2O/Et_2NH/MeOH$ (50:50:5:10) | Diastereoisomer 1 - white solid, m.p. 206–208° C.<br><br><br>Analysis %:-<br>Found: C, 69.00; H, 7.08; N, 10.83<br>$C_{22}H_{27}N_3O_3$<br>requires: C, 69.27; H, 7.14; N, 11.02<br>Diastereoisomer 2 - yellow oil,<br>$^1$H-NMR(300MHz, $CDCl_3$)δ=1.2–1.9(m, 6H), 2.4–2.9(m, 8H), 3.2(m, 1H), 4.1(d, 1H), 4.3(d, 1H), 4.9(m, 1H), 7.2–7.5(m, 6H), 9.0(m, 2H)ppm.<br>Mass spectrum: m/e (MH$^+$) = 382 |

-continued

| Example No. | Het, base | Experimental Variations | Analytical Data |
|---|---|---|---|
| 34 | ![structure with O-N, N, Me] (prepared as described in Helv. Chim. Acta. 441, 45, 1962); lithium diisopropylamide | Anion generated totally at −78° C. | Diastereoisomer 1 - white solid, m.p. 164–166° C.<br><br>Analysis %:-<br>Found: C, 65.09; H, 7.01; N, 10.76<br>$C_{21}H_{27}N_3O_4$<br>requires: C, 65.44; H, 7.06; N, 10.90<br>Diastereoisomer 2 - white solid, m.p. 155–157° C.<br>Analysis %:-<br>Found: C, 65.54; H, 7.02; N, 10.77<br>$C_{21}H_{27}N_3O_4$<br>requires: C, 65.44; H, 7.06; N, 10.90 |

EXAMPLE 35

(R)-3-Quinuclidinyl (R and S)-2-hydroxymethyl-2-phenyl-4-(1H-pyrazol-1-yl)butanoate

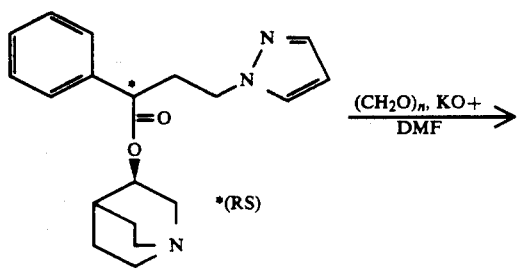

(R)-3-Quinuclidinyl (RS)-2-phenyl-4-(1H-pyrazol-1-yl)butanoate (see Preparation 13) (0.3 g) was added to a mixture of paraformaldehyde (40 mg) and potassium tert-butoxide (30 mg) that had been pre-stirred in dimethylformamide (15 ml) for ¼ hour at room temperature. After 1 hour the mixture was partitioned between 10% aqueous sodium carbonate and ethyl acetate. The organic layer was dried over magnesium sulphate and evaporated to give a residue which was purified by chromatography on silica gel performing a gradient elution using ethyl acetate/ether/diethulamine (50:50:5) plus methanol (5–10%) as the eluant. Appropriate fractions were combined and evaporated to give the two title compounds, of undefined stereochemistry, as white solids.

Diastereoisomer 1 (higher Rf by tlc) (29 mg, 18% based on single isomer). m.p. 154°–156° C.

Analysis %: Found: C, 68.16; H, 7.39; N, 11.20; $C_{21}H_{27}N_3O_3$ requires: C, 68.27; H, 7.37; N, 11.37.

Diastereoisomer 2 (lower Rf by tlc) (23 mg, 14.4% based on single isomer), m.p. 138°–140° C.

Analysis %: Found: C, 68.61; H, 7.40; N, 11.31; $C_{21}H_{27}N_3O_3$ requires: C, 68.27; H, 7.37; N, 11.37.

EXAMPLE 36

(R)-3-Quinuclidinyl (R and S)-2-hydroxymethyl-2-phenyl-4-(1H, 1,2,4-triazol-1-yl)butanoate

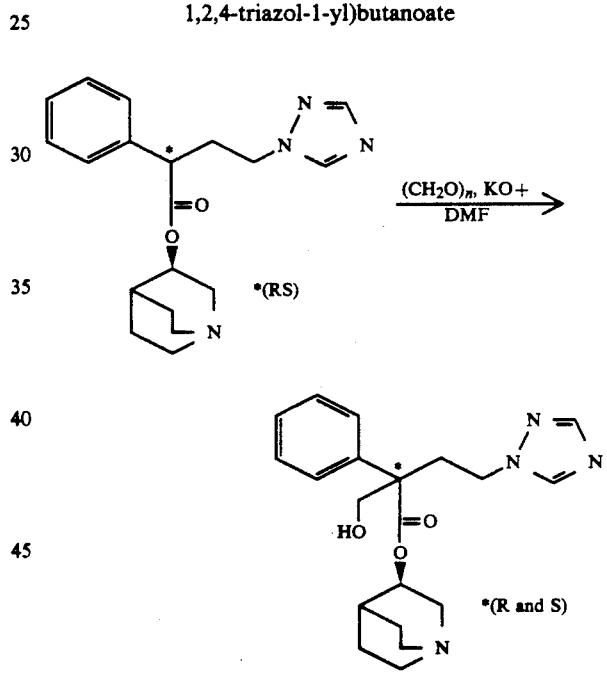

the title compounds, of undefined stereochemistry, were obtained as white solids, by a similar method to that described in Example 35 using (R)-3-quinuclidinyl (RS)-2-phenyl-4-(1H, 1,2,4-triazol-1-yl)butanoate (see Preparation 14) in place of (R)-3-quinuclidinyl (R,S)-2-phenyl-4-(1H-pyrazol-1-yl)butanote.

Diastereoisomer 1 (higher Rf by tlc) (18% based on single isomer) m.p. 182°–184° C.

Analysis %: Found: C, 64.08; H, 6.82; N, 14.52 $C_{20}H_{26}N_4O_3.\frac{1}{4}H_2O$ requires: C, 64.07; H, 7.13; N, 14.94

Diastereoisomer 2 (lower Rf by tlc) (14.6% based on single isomer) m.p. 140°–142° C.

$^1$H-NMR (300 MHz, CDCl$_3$), δ=1.2–1.5 (m, 1H), 1.5–19 (m, 3H), 2.05 (m, 1H), 2.6–3.1 (m, 7H), 3.3 (m, 1H), 4.0 (d, 1H), 4.2 (m, 2H), 4.4 (d, 1H), 4.9 (m, 1H), 7.2–7.5 (m, 5H), 8.0 (d, 2H).

Mass spectrum: m/e (MH+)=371.5

EXAMPLE 37

(R)-3-Quinuclidinyl (R and S)-2-hydroxymethyl-2-phenyl-4-(2-methyl-tetrazol-5-yl)butanoate

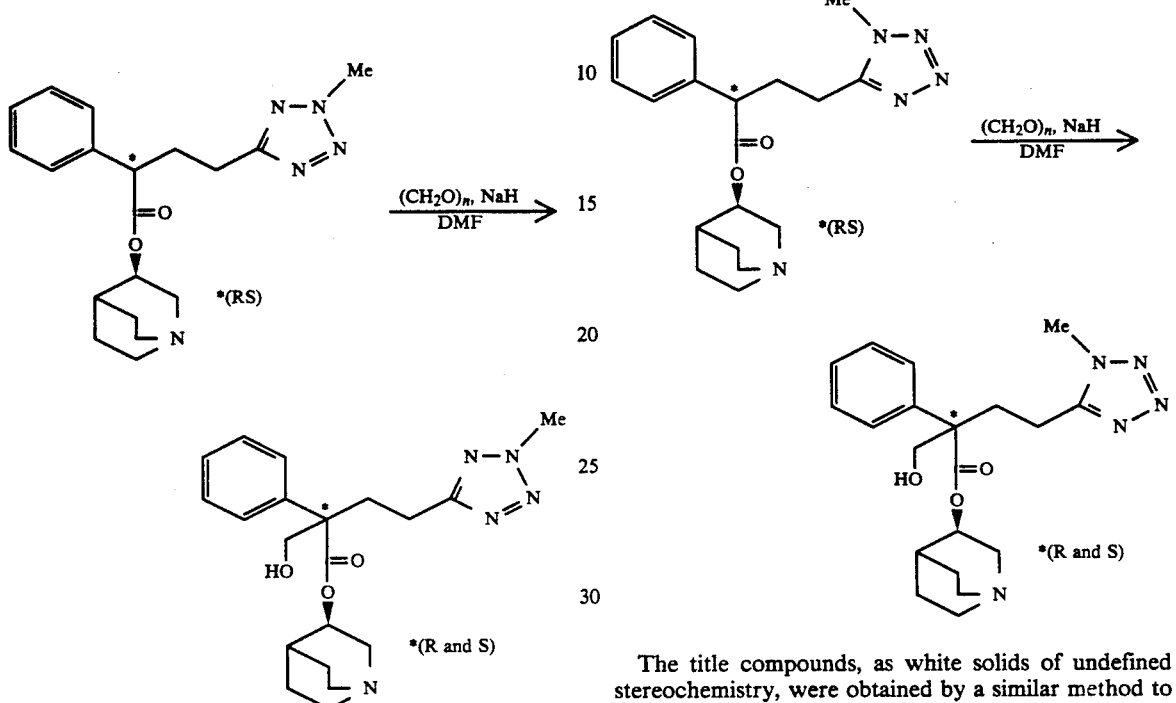

Sodium hydride (32 mg, as an 80% dispersion in oil) and paraformaldehyde (0.1 g) in dimethylformamide (5 ml) were stirred at room temperature for ¼ hour. (R)-3-Quinuclidinyl (RS)-2-phenyl-4-(2-methyl-tetrazol-5-yl)butanoate (see Preparation 15) (0.38 g) in dimethylformamide (5 ml) was added, the mixture stirred for ½ hour, evaporated, and the residue partitioned between ethyl acetate and water. The organic layer was dried over magnesium sulphate and evaporated to give a residue which was purified by chromatography on silica gel using ethyl acetate/ether/diethylamine/methanol (50:50:5:10) as the eluant. Appropriate fractions were combined and evaporated to give the two title compounds of undefined stereochemistry, as white solids.

Diastereoisomer 1 (higher Rf by tlc) (49 mg, 29% based on single isomer) m.p. 172°–174° C.

Analysis %: Found: C, 62.55; H, 6.73; N, 17.86 $C_{20}H_{27}N_5O_3$ requires: C, 62.32; H, 7.06; N, 18.17

Diastereoisomer 2 (lower Rf by tlc) (36 mg, 21% based on single isomer) m.p. 168°–170° C.

Analysis %: Found: C, 62.56; H, 7.06; N, 18.16 $C_{20}H_{27}N_5O_3$ requires: C, 63.32; H, 7.06; N, 18.17

EXAMPLE 38

(R)-3-Quinuclidinyl (R and S)-2-hydroxymethyl-2-phenyl-4-(1-methyl-tetrazol-5-yl)butanoate

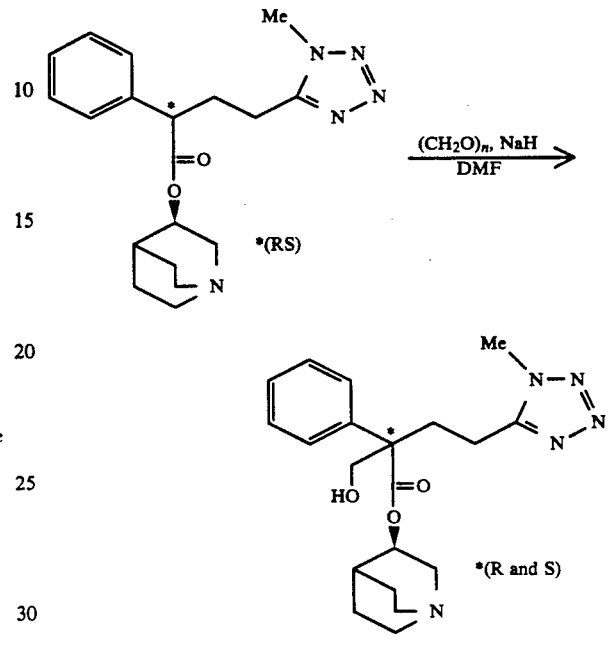

The title compounds, as white solids of undefined stereochemistry, were obtained by a similar method to that described in Example 37 using (R)-3-quinuclidinyl (RS)-2-phenyl-4-(1-methyl-tetrazol-5-yl)butanoate (see Preparation 16) in place of R-3-quinuclidinyl (RS)-2-phenyl-4-(2-methyltetrazol-5-yl)butanoate.

Diastereoisomer 1 (higher Rf by tlc) (30% based on single isomer) m.p. 199°–200° C.

Analysis %: Found: C, 62.41; H, 7.05; N, 18.00 $C_{20}H_{27}N_5O_3$ requires: C, 62.32; H, 7.06; N, 18.17

Diastereoisomer 2 (lower Rf by tlc) (23% based on single isomer) m.p. 186°–188° C.

Analysis %: Found: C, 62.27; H, 7.14; N, 17.77 $C_{20}H_{27}N_5O_3$ requires: C, 62.32; H, 7.06; N, 18.17

The following Preparations illustrate the preparation of novel starting materials used in the previous Examples:

PREPARATION 1

(R)-3-Quinuclidinyl 2-phenylacrylate

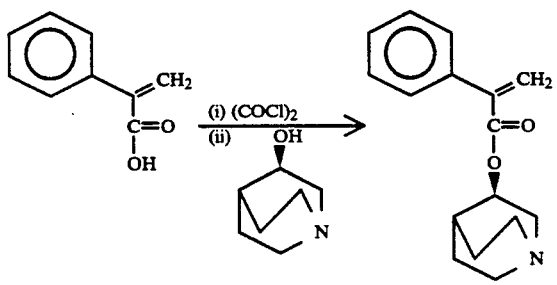

Oxalyl chloride (44.2 ml) was added to a solution of 2-phenylacrylic acid (50 g) (prepared as described in J. Chem. Soc., 2557, 123, 1923) and dimethylformamide (½ ml) in chloroform (500 ml). The mixture was stirred for ¼ hour. dimethylformamide (¼ ml) was added and the mixture was stirred for a further ¼ hour, then evaporated to give a residue to which chloroform (2×100 ml) was added and then evaporated. The residue was finally dissolved in chloroform (500 ml) and to this solution at 10°–15° C. was added (R)-3-quinuclidinol (prepared as described in Acta. Pharm. Suec: 281, 16, 1979) dissolved in chloroform (500 ml). The mixture was stirred for ¼ hour, allowed to slowly reach room temperature, evaporated and the residue partitioned between 25% aqueous potassium carbonate and ether. The organic layer was dried over magnesium sulphate, evaporated and the residue recrystallised from hexane to give the title compound as a white solid (66 g, 76%, m.p. 83°–85° C.

Analysis %:
Found: C, 74.39; H, 7.47; N, 5.45; $C_{16}H_{19}NO_2$ requires: C, 74.67; H, 7.44; N, 5.44.

PREPARATION 2

(R)-3-Quinclidinyl 2-phenylglyoxalate

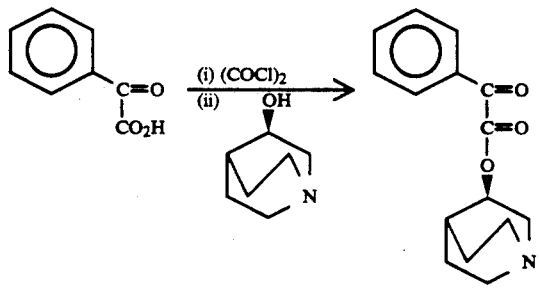

Oxalyl chloride (13.7 ml) was added to a solution of phenylglyoxylic acid (19.7 g) and dimethylformamide (2 drops) in chloroform (160 ml). After 2 hours the solvent was evaporated, the residue dissolved in chloroform (120 ml) and (R)-3-quinuclidinol (20 g) in chloroform (200 ml) was added to this at 0° C. The mixture was stirred at room temperature for 2 hours, washed with 10% aqueous potassium carbonate, then with water, dried over sodium sulphate and evaporated to leave the title compound, as a yellow oil, (27 g, 64%).

$^1$H-NMR (300 MHz, $CDCl_3$) δ=1.4–2.0 (m, 4H), 2.25 (s, 1H), 2.8–3.6 (m, 6H), 5.2 (m, 1H), 7.2–7.8 (m, 3H), 8.0–8.2 (m, 2H) ppm.

PREPARATION 3

(R)-3-Quinuclidinyl (RS)-2-hydroxy-2-phenyl-3-(pyrazin-2-yl)propanoate

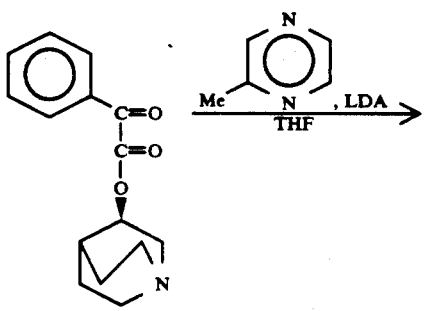

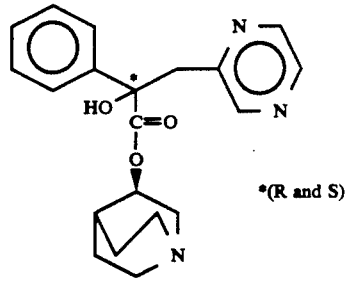

*(R and S)

2-Methylpyrazine (0.94 g) in tetrahydrofuran (THF) (5 ml) was added dropwise to lithium diisopropylamide (LDA) (7.51 ml of a 1.5 molar solution in THF) in THF (20 ml) at −78° C. After 0.75 hour a solution of (R)-3-quinuclidinyl 2-phenylglyoxalate (see Preparation 2) (2.59 g) in THF (20 ml) was added, the reaction mixture was allowed to reach room temperature, stirred for 1 hour and partitioned between ethyl acetate and 10% aqueous potassium carbonate. The organic layer was then dried over magnesium sulphate and evaporated to leave a residue which was purified by chromatography on silica gel performing a gradient elution using chloroform plus methanol (0→15%). Appropriate fractions were combined and evaporated to give the title compound, as a yellow oil (1.4 g, 39%).

$^1$H-NMR (300 MHz, $CDCl_3$) δ=1.2–2.0 (m, 5H), 2.6–2.9 (m, 5H), 3.1 (m, 1H), 3.4 (d, 1H), 3.9 (d, 1H), 4.8 (m, 1H), 7.35 (m, 3H), 7.65 (m, 2H), 8.4 (m, 2H), 8.55 (s, 1H) ppm.

PREPARATION 4

(R)-3-Quinuclidinyl 2-phenyl-3-(pyrazin-2-yl)acrylate

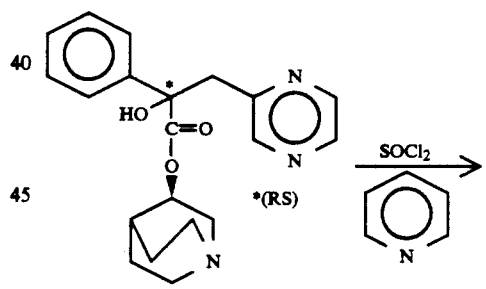

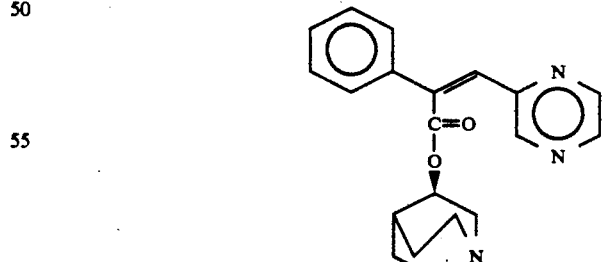

Thionyl chloride (0.534 ml) in chloroform (5 ml) was added at 0° C. to a solution of (R)-3-quinuclidinyl (RS)-2-hydroxy 2-phenyl-3-(pyrazin-2-yl)propanoate (see Preparation 3) (1.3 g) in chloroform (5 ml). After 10 minutes, pyridine (0.6 ml) in chloroform (5 ml) was added and the mixture was stirred for 24 hours, diluted with chloroform, washed with 10% aqueous potassium carbonate, dried over magnesium sulphate and evaporated. The residue was then purified by chromatography on silica gel performing a gradient elution using chloroform plus methanol (0→10%) and ammonia solution (0→1%). Appropriate fractions were combined and evaporated to give the title compound as an off-white solid (0.4 g, 32%) m.p. 125°-126° C.

¹H-NMR (30 MHz, CDCl₃) δ=1.2-1.8 (m, 4H), 2.2 (s, 1H), 2.8 (m, 4H), 3.15 (d, 1H), 3.4 (m, 1H), 5.2 (m, 1H), 7.0 (s, 1H), 7.3-7.6 (m, 5H), 8.2 (s, 1H), 8.55 (s, 1H), 8.6 (s, 1H) ppm.

PREPARATION 5

(R)-3-Quinuclidinyl (RS)-2-phenyl-3-(pyrazin-2-yl)propanoate

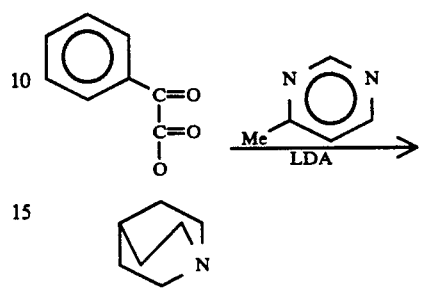

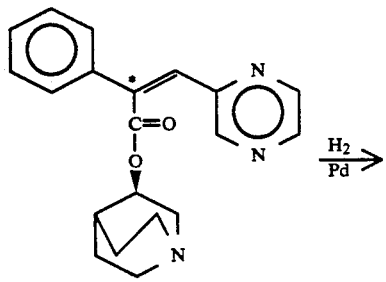

A solution of (R)-3-quinuclidinyl 2-phenyl-3-(pyrazin-2-yl)acrylate (see Preparation 4) (350 mg) in ethanol (20 ml) containing 10% palladium-on-carbon (30 mg) was stirred for 24 hours under an atmosphere of hydrogen [344.7 kPa (50 psi)] at room temperature. The mixture was filtered and evaporated to leave the title compound as an oil (320 mg, 91%).

¹H-NMR (300 MHz, CDCl₃) δ=1.2-2.1 (m, 5H), 2.5-3.0 (m, 5H), 3.2 (m, 2H), 3.7 (m, 1H), 4.3 (m, 1H), 4.95 (m, 1H), 7.2-7.5 (m, 5H), 8.4 (s, 2H), 8.55 (d, 1H) ppm.

PREPARATION 6

(R)-3-Quinuclidinyl (RS)-2-hydroxy-2-phenyl-3-(pyrimidin-4-yl)propanoate

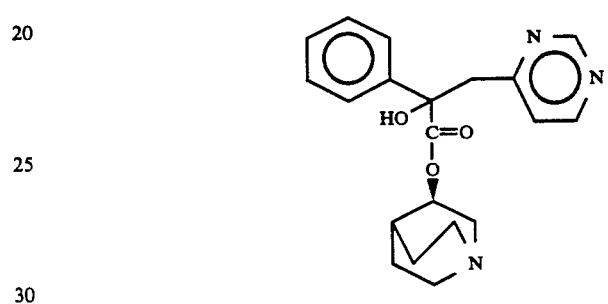

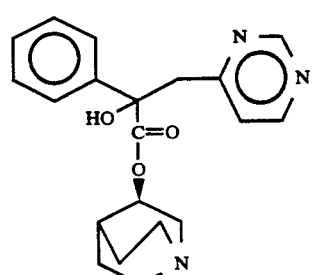

The title compound, as an oil, (66%) was prepared by a similar method to that described in Preparation 3 using 4-methylpyrimidine in place of 2-methylpyrazine.

¹H-NMR (300 MHz, CDCl₃) δ=1.2-2.4 (m, 5H), 2.5-3.0 (m, 5H), 3.15 (m, 1H), 3.4 (m, 1H), 3.9 (m, 1H), 4.8 (m, 1H), 7.2-7.7 (m, 6H), 8.6 (m, 1H), 9.1 (s, 1H) ppm.

PREPARATION 7

(R)-3-Quiniclidinyl 2-phenyl-3-(pyrimidin-4-yl)acrylate

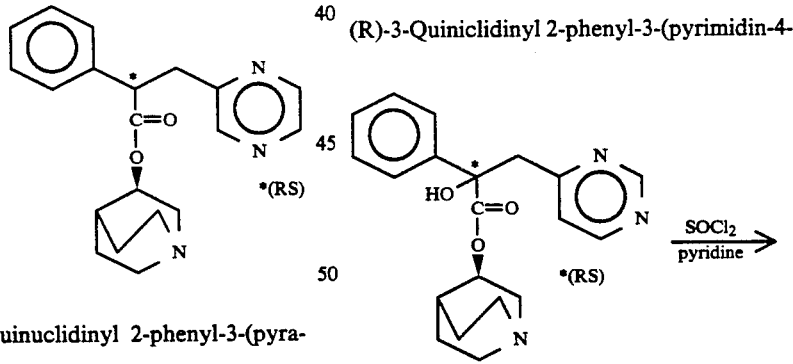

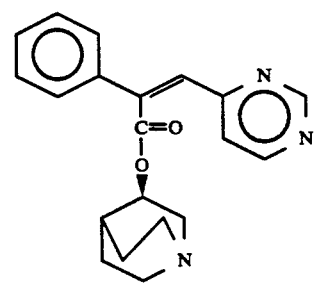

The title compound, as a brown solid (97%) was prepared by a similar method to that described in Preparation 4 using (R)-3-quinuclidinyl (RS)-2-hydroxy-2-phenyl-3-(pyrimidin-4-yl)propanoate (see Preparation 6) instead of (R)-3-quinuclidinyl (RS)-2-hydroxy-2-phenyl-3-(pyrazin-2-yl)propanoate.

¹H-NMR (300 MHz, CDCl₃) δ=(m, 1H), 3.35 (m, 1H), 5.2 (m, 1H), 6.8 (s, 1H), 7.3 (s, 1H), 7.4–7.6 (m, 5H), 8.7 (d, 1H), 9.05 (s, 1H) ppm.

PREPARATION 6

(R)-3-Quinuclidinyl (RS)-2-phenyl-3-(pyrimidin-4-yl)propanoate

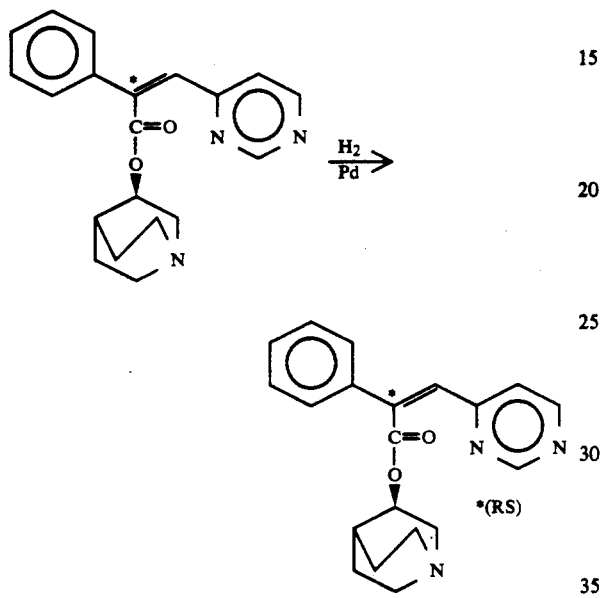

The title compound, as an oil, (95%) was prepared by a similar method to that described in Preparation 4 using (R)-3-quinuclidinyl-2-phenyl-3-(pyrimidin-4-yl)acrylate (see Preparation 7) instead of (R)-3-quinuclidinyl-2-phenyl-3-(pyrazin-2-yl)acrylate.

¹H-NMR (300 MHz, CDCl₃) δ=1.6–2.4 (m, 5H), 2.8–3.7 (m, 6H), 4.1 (m, 2H), 4.7 (m, 1H), 5.2 (m, 1H), 7.5 (m, 1H), 7.7 (m, 5H), 8.9 (d, 1H), 9.4 (d, 1H) ppm.

Mass spectrum: m/e (M⁺)=337

PREPARATION 9

(R)-3-Quinuclidinyl 2-phenylacetate

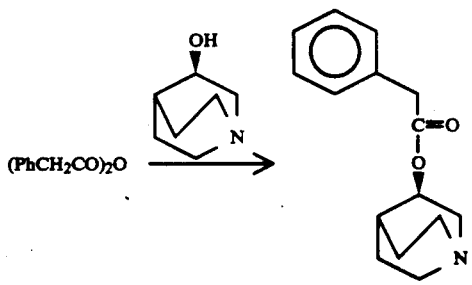

Phenylacetic acid anhydride (prepared as described in J. Org. Chem., 1588, 30, 1965) (15 g) was added to a suspension of (R)-3-quinuclidinol (5 g) in ethyl acetate (250 ml) at room temperature. After 178 hour the solvent was evaporated and the residue dissolved in hydrochloric acid (2M). This was washed with ethyl acetate, basified with sodium carbonate and extracted with ethyl acetate. The organic extract was dried over sodium sulphate and evaporated to give the title compound as a yellow oil (9 g, 66%).

Analysis %: Found: C, 72.95; H, 7.69; N, 5.43; C₁₅H₁₉NO₂ requires: C, 73.44, H, 7.81; N, 5.71.

PREPARATION 10

(R)-3-Quinuclidinyl (RS)-2-phenyl-3-(pyridin-2-yl)propanoate

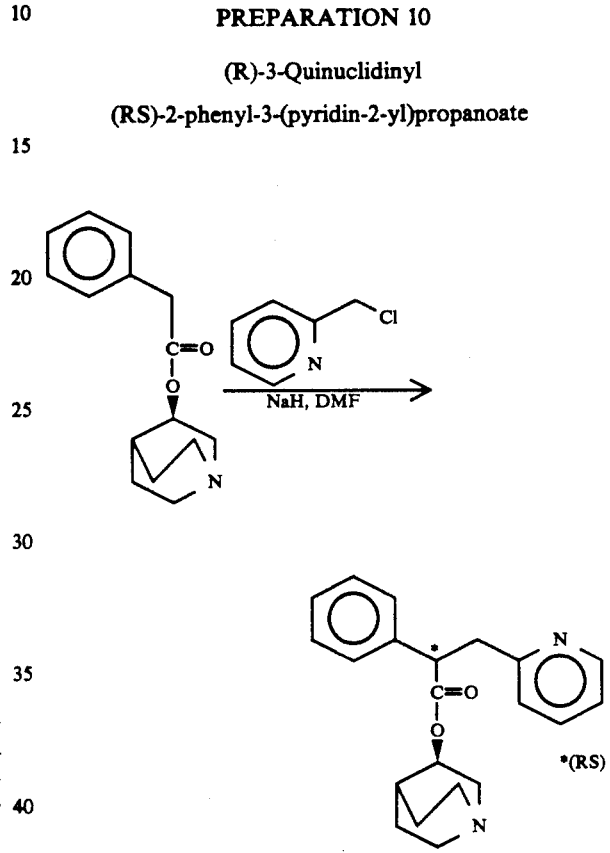

A mixture of (R)-3-quinuclidinyl 2-phenylacetate (see Preparation 9) 1.23 g) and sodium hydride (165 mg of an 80% dispersion in oil) in dimethylformamide (10 ml) was stirred for ¼ hour, treated with 2-picolyl chloride (0.64 g), stirred for 24 hours then partitioned between ethyl acetate and 10% aqueous potassium carbonate. The organic layer was dried over magnesium sulphate and the residue, after evaporation, was purified by chromatography on silica gel by gradient elution using chloroform plus methanol (0→10%) and aqueous ammonia (0→1%). Appropriate fractions were combined and evaporated to give the title compound as an oil (605 mg, 36%).

¹H-NMR (300 MHz, CDCl₃) δ=1.1–2.9 (m, 5H), 2.2–3.0 (m, 5H), 3.2 (m, 2H), 3.65 (m, 1H), 4.3 (m, 1H), 4.7 (m, 1H), 7.0–7.6 (m, 8H), 8.5 (m, 1H) ppm.

PREPARATION 11

(R)-3-Quinuclidinyl
(RS)-2-phenyl-3-(pyridin-3-yl)propanoate

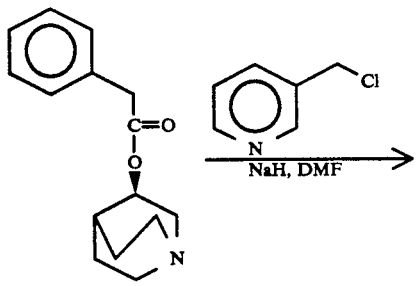

The title compound, as an oil, (73%) was prepared by a similar method to that described in Preparation 10 using 3-picolyl chloride in place of 2-picolyl chloride.

¹H-NMR (300 MHz, CDCl₃) δ=1.2–1.8 (m, 4H), 1.8 (m, 1H), 2.5–2.8 (m, 5H), 3.1 (m, 1H), 3.25 (m, 1H), 3.85 (m, 1H), 4.75 (m, 1H), 7.2–7.6 (m, 7h), 8.45 (m, 2H) ppm.

Mass spectrum: m/e (M+)=336

PREPARATION 12

(R)-3-Quinuclidinyl
(RS)-2-phenyl-3-(pyridin-4-yl)propanoate

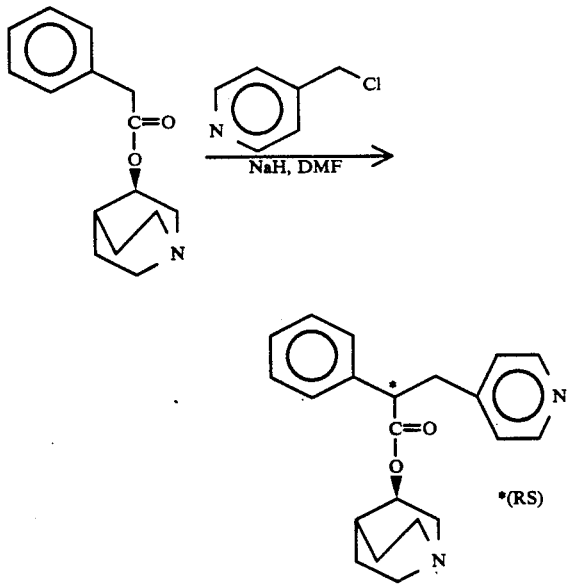

The title compound, as an oil, (25%) was prepared by a similar method to that described in Preparation 10 using 4-picolyl chloride in place of 2-picolyl chloride followed by purification of the crude product by silica gel chromatography eluting with ethyl acetate/ether/diethylamine/methanol (50:50:2½:2½).

¹H-NMR (300 MHz, CDCl₃)=1.2–1.8 (m, 4H), 1.9 (s, 1H), 2.4–2.8 (m, 5H), 3.1 (m, 2H), 3.45 (m, 1H), 3.9 (m, 1H), 4.7 (m, 1H), 7.1 (d, 2H), 7.2–7.5 (m, 5H), 8.5 (d, 2H) ppm.

Mass Spectrum m/e (M+)=336

PREPARATION 13

(R)-3-Quinuclidinyl
(RS)-2-phenyl-4-(1H-pyrazol-1-yl)butanoate

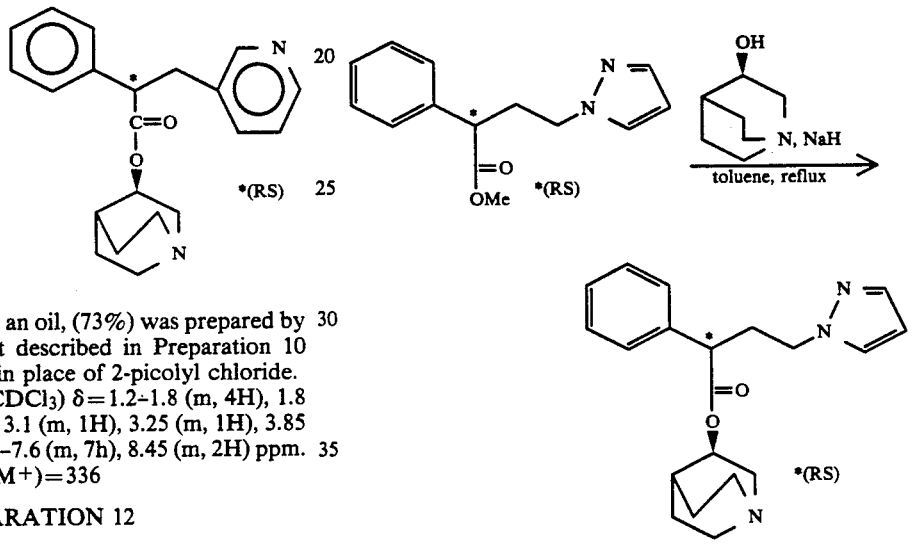

A mixture of methyl (RS)-2-phenyl-4-(1H-pyrazol-1-yl)butanoate (see Preparation 17) (0.37 g), (R)-3-quinuclidinol (0.24 g) sodium hydride (15 mg, as an 80% dispersion in oil) in toluene (15 ml) as refluxed with continuous removal of distillate and, when necessary, replacement with fresh toluene, for 1½ hours. The cooled mixture was successively washed with water then saturated brine and extracted with 2M hydrochloric acid. The aqueous layer was washed with ethyl acetate, basified with potassium carbonate and extracted with ethyl acetate. The organic layer was dried over magnesium sulphate and evaporated to give the title compound (0.31 g, 61%) as a yellow oil ¹H-NMR (300 MHz, CDCl₃)δ=1.0–2.0 (m, 5H), 2.2–2.8 (m, 7H), 3.1 (m, 1H), 3.5 (t, 1H), 4.1 (m, 2H), 4.8 (m, 1H), 6.25 (s, 1H), 7.2–7.4 (m, 6H), 7.55 (s, 1H) ppm.

Mass spectrum: m/e (M+)=339

PREPARATIONS 14–16

The following tabulated examples of the general formula:

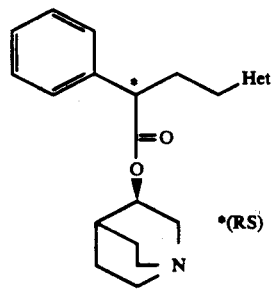

were obtained by similar methods to that described in Preparation 13 by ester exchange using the appropriately substituted methyl butanoate and (R)-3-quinuclidinol.

| Preparation No. | —Het | Analytical Data |
|---|---|---|
| 14 | (See preparation 18 for starting material) | Colourless oil, $^1$H-NMR(300MHz, CDCl$_3$), δ=1.1–2.0 (m, 5H), 2.2–2.8(m, 7H), 3.2(m, 1H), 3.5 (m, 1H), 4.15(m, 2H), 4.8(m, 1H), 7.1–7.5(m, 6H), 8.0 (d, 1H)ppm. |
| 15 | (See Preparation 19 for starting material) | Colourless oil, $^1$H-NMR(300MHz, CDCl$_3$), δ=1.0–2.0 (m, 5H), 2.0–3.0(m, 9H), 3.2(m, 1H), 3.7 (t, 1H), 4.3(s, 3H), 4.8(m, 1H), 7.2–7.5 (m, 5H)ppm. |
| 16 | (See preparation 19 for starting material) | Colourless oil, $^1$H-NMR(300MHz, CDCl$_3$), δ=1.0–2.0 (m, 5H), 2.0–3.0(m, 9H), 3.2(m, 1H), 3.8 (t, 1H), 3.95(s, 3H), 4.8(m, 1H), 7.2–7.5(m, 5H)ppm. |

PREPARATION 17

Methyl (RS)-2-phenyl-4-(1H-pyrazol-1-yl)butanoate

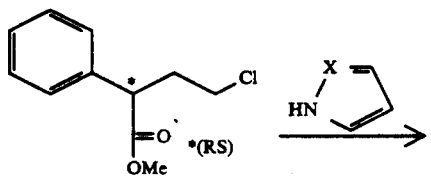

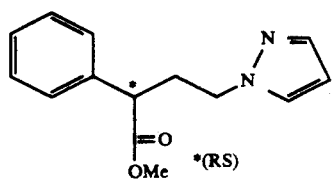

Methyl (RS)-4-chloro-2-phenylbutanoate (prepared as described in J. Amer. Chem. Soc., 443, 73, 1951) (1 g) and pyrazole (1 g) were heated together at 120° C. for 5 hour, cooled and the residue partitioned between ether and water. The organic layer was washed with water and extracted with 2M hydrochloric acid. The acid extracts were basified with sodium carbonate and extracted with ether. The organic layer was dried over magnesium sulphate and evaporated to give the title compound (0.37 g, 33%) as a colourless oil.

$^1$H-NMR (300 MHz, CDCl$_3$), =2.35 (m, 1H), 2.7 (m, 1H), 3.5 (t, 1H), 3.7 (s, 3H), 4.1 (m, 2H), 6.3 (s, 1H), 7.2–7.5 (m, 6H), 7.6 (s, 1H) ppm.

PREPARATION 18

Methyl (RS)-2-phenyl-4-(1H-1,2,4-triazol-1-yl)butanoate

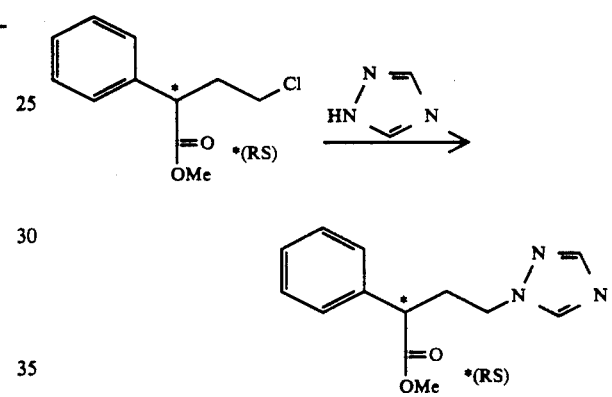

The title compound, as a colourless oil, was prepared in 31% yield by a similar method to that described in Preparation 17 using 1,2,4-triazole in place of pyrazole.

$^1$H-NMR (300 MHz, CDCl$_3$), =2.2 (m, 1H), 2.7 (m, 1H), 3.5 (t, 1H), 3.7 (s, 3H), 4.15 (m, 2H), 7.2–7.5 (m, 6H), 8.0 (s, 1H) ppm.

PREPARATION 19

Methyl (RS)-2-phenyl-4-(2-methyl-tetrazol-5-yl)butanoate and methyl (RS)-2-phenyl-4-(1-methyl-tetrazol-5-yl)butanoate

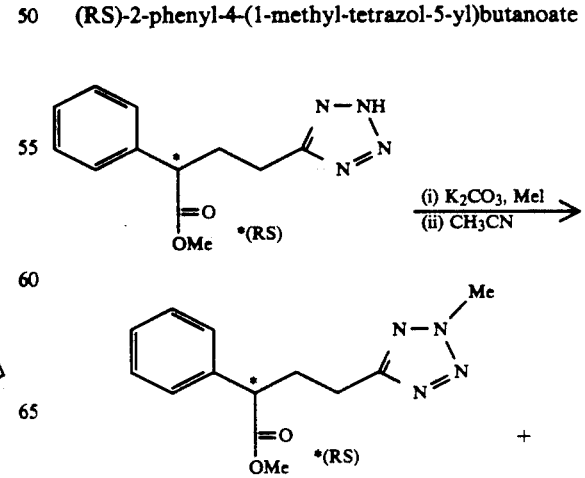

-continued

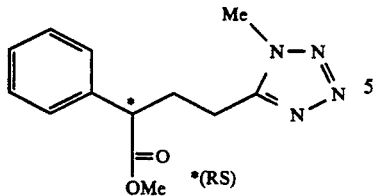

Methyl iodide (0.34 ml) was added to a mixture of potassium carbonate (1.13 g) and methyl (RS)-2-phenyl-4-(1H-tetrazol-5-yl)butanoate (see Preparation 20) (1.34 g) in acetaonitrile (50 ml). After 18 hours the mixture was filtered and the filtrate evaporated to leave a residue which was partitioned between 10% aqueous potassium carbonate and ether. The organic layer was dried over magnesium sulphate and evaporated to leave a residue which was purified by chromatography on silica gel eluting with ethyl acetate/hexane (40:60). Appropriate fractions were combined and evaporated to give to two title compounds, as colourless oils.

2-Methyltetrazol-5-yl isomer (higher Rf on tlc) (0.38 g. 27%)

$^1$H-NMR (300 MHz, CDCl$_3$), $\delta$=2.3 (m, 1H), 2.55 (m, 1H), 2.85 (m, 2H), 3.7 (m, 4H), 4.3 (s, 3H), 7.3 (m, 5H) ppm.

1-Methyltetrazol-5-yl isomer (lower Rf on tlc) (0.51 g, 36%)

$^1$H-NMR (300 MHz, CDCl$_3$), $\delta$=2.3 (m, 1H, 2.55 (m, 1H), 2.8 (m, 2H), 3.65 (s, 3H), 3.75 (t, 1H), 3.9 (s, 3H), 7.2-7.5 (m, 5H) ppm.

PREPARATION 20

Methyl (RS)-2-phenyl-4-(1H-tetrazol-5-yl)butanoate

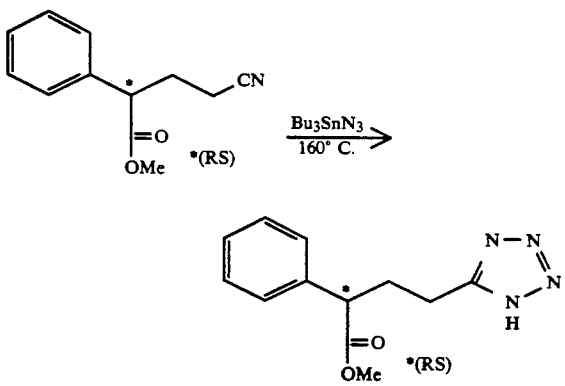

Methyl (RS)-4-cyano-2-phenylbutanoate (see Preparation 21) (1.8 g) and tri-n-butyltin azide (3.23 g were mixed and heated at 160° C. for 3 hours, dissolved in methanol (100 ml), treated by the addition of hydrogen chloride gas for 10 minutes and left for 18 hours. Evaporation gave a residue which was triturated three times with diisopropyl ether then partitioned between 10% aqueous sodium carbonate and ethyl acetate. The aqueous later was acidifed with 2 M hydrochloric acid and extracted with ethyl acetate. The organic layer was dried over magnesium sulphate and evaporated to give the title compound (1.34 g, 61%) as a brown oil.

$^1$H-NMR (300 MHz, CDCl$_3$),=2.35 (m, 1H), 2.45 (m, 1H), 3.05 (t, 2H), 3.65 (s, 3H), 3.75 (t, 1H), 7.2-7.5 (m, 5H) ppm.

PREPARATION 21

Methyl (RS)-4-cyano-2-Phenylbutanoate

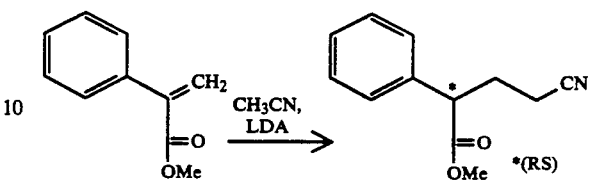

Lithium diisopropylamide (3.67 ml of a 1.5 molar solution in cyclohexane) was added to acetonitrile (0.26 ml) in tetrahydrofuran (10 ml) at $-78°$ C. After 1 hour, methyl 2-phenyl-acrylate (see Preparation 22) (0.81 g) in tetrahydrofurn (10 ml) was added and the mixture was stirred for 1 hour, allowed to warm to room temperature then treated with saturated ammonium chloride solution. The resulting mixture was partitioned between ethyl acetate and water, the organic phase dried over magnesium sulphate and evaporated to give a residue which was partitioned between ether and 10% aqueous sodium carbonate. The organic layer was dried over magnesium sulphate and evaporated to leave the title compound (0.5 g, 75%) as an oil.

$^1$H-NMR (300 MHz, CDCl$_3$), $\delta$=2.0–2.4 (m, 4H), 3.7 (s, 3H), 3.8 (t, 1H), 7.2-7.5 (m, 5H) ppm. I.R. (thin film) 2220 cm$^{-1}$ (C≡N).

PREPARATION 22

Methyl 2-phenylacrylate

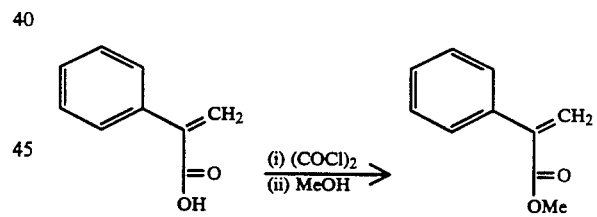

Oxalyl chloride (24 ml) was added to a solution of 2-phenyl-acryclic acid (37 g) and dimethylformamide (0.5 ml) in dichloromethane (400 ml). The mixture was stirred for 1 hour and then evaporated to give a residue to which dichloromethane (50 ml) was added and evaporated. Methanol (200 ml) was added to the residue, which was then stirred for 1 hour and evaporated to give a residue which was partitioned between 10% aqueous sodium bicarbonate and hexane. The organic layer was dried over magnesium sulphate and evaporated to give the title compound as a colourless oil (39.2 g, 97%).

$^1$H-NMR (300 MHz, CDCl$_3$), $\delta$=3.9 (s, 3H), 5.9 (s, 1H), 6.4 (s, 1H), 7.2-7.5 (m, 5H).

I claim:

1. A compound of the formula:

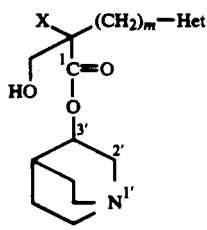

or a pharmaceutically acceptable salt thereof, wherein X is either (a) a phenyl group optionally substituted by 1 or 2 substituents each independently selected from halo, $CF_3$, $C_1-C_4$ alkyl, $C_1-C_4$ alkoxy and hydroxy or (b) a thienyl group; and "Het" is either (a) a 5-membered nitrogen containing heterocyclic group attached to the adjacent carbon atom either by a carbon or a ring nitrogen atom and which is selected from imidazolyl, pyrazolyl, triazolyl and tetrazolyl, (b) an oxadiazolyl or thiadiazolyl group attached to the adjacent carbon atom by a carbon atom, or (c) a pyridinyl group attached to the adjacent carbon atom by a carbon atom, "Het" being optionally substituted by up to 2 substituents each independently selected from halo, $CF_3$, $C_1-C_4$ alkyl, $C_1-C_4$ alkoxy, hydroxy, amino and azido; and m is 1 or 2.

2. A compound as claimed in claim 1, wherein "Het" is an imidazolyl, pyrazolyl, triazolyl, tetrazolyl, oxadiazolyl, or pyridinyl group, all said groups being optionally substituted by one or two substituents selected from $C_1-C_4$ alkyl and halo.

3. A compound as claimed in claim 1, wherein "Het" is 1H-imidazol-1-yl, 2-azido-1H-imidazol-1-yl, 2-amino-1H-imidazol-1-yl, 2-methyl-1H-imidazol-1-yl, 4-methyl-1H-imidazol-1-yl, imidazol-2-yl, 1-methylimidazol-2-yl, 1H-1,2,3-triazol-1-yl, 1-methyl-1,2,3-triazol-5-yl, 1H-1,2,4-triazol-1-yl, 3-bromo-5-(methyl, ethyl, propyl, isopropyl or isobutyl)-1H-1,2,4-triazol-1-yl, 5-(methyl, ethyl, propyl, isopropyl or isobutyl)-1H-1,2,4-triazol-1-yl, 3-chloro-1H-1,2,4-triazol-1-yl, 1H-1,2,5-triazol-1-yl, 1H-tetrazol-1-yl, 1-methyl-tetrazol-5-yl, 2-methyl-tetrazol-5-yl, 1H-imidazol-4(5)-yl, pyridin-2-, 3- or 4-yl, or 3-methyl-1,2,4-oxadiazol-5-yl.

4. A compound as claimed in claim 3, wherein either (a) m is 1 and "Het" is a 1H-imidazol-1-yl, 1H-1,2,4-triazol-1-yl or 5-methyl-1H-1,2,4-triazol-1-yl group or (b) m is 2 and "Het" is a 1-methylimidazol-2-yl group.

5. A compound as claimed in claim 1 in which X is either (a) a phenyl group optionally substituted by 1 or 2 fluoro atoms or (b) a 3-thienyl group.

6. A compound as claimed in claim 5 where X is an unsubstituted phenyl group.

7. A compound as claimed in claim 1 in which either (a) m is 1 and the compound is in the (2R, 3R) form or (b) m is 2 and the compound is in the (2S, 3R) form.

8. A compound as claimed in claim 1 in which m is 1 and "Het" is as defined in parts (a) and (c) of claim 1.

9. A compound as claimed in claim 1 in which m is 2.

10. A pharmaceutical composition comprising a compound of the formula (I) as claimed in any one of the preceding claims, or a pharmaceutically acceptable salt thereof, and a pharmaceutically acceptable diluent or carrier.

11. A compound of the formula:

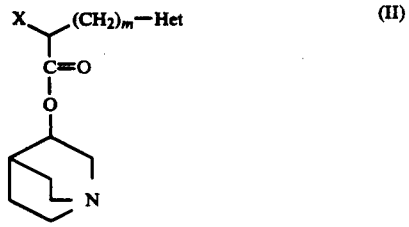

or a salt thereof with a strong base, where X, Het and m are as defined in claim 1.

12. A compound of the formula:

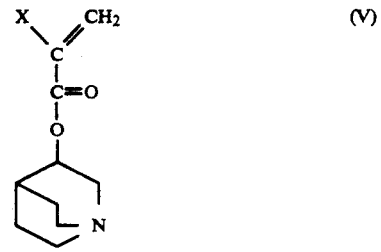

where X is as defined in claim 1.

13. A method of treating chronic obstructive airways disease or asthma in a patient in need of such treatment, which comprises administering to said patient an effective amount of a compound of the formula (I) or pharmaceutically acceptable salt thereof, as claimed in claim 1.

14. A pharmaceutical composition for treating chronic obstructive airways disease or asthma comprising an effective amount of a compound according to claim 1 and a pharmaceutically acceptable carrier.

* * * * *